United States Patent [19]
Singh et al.

[11] Patent Number: 5,102,872
[45] Date of Patent: Apr. 7, 1992

[54] CONTROLLED-RELEASE FORMULATIONS OF INTERLEUKIN-2

[75] Inventors: Maninder Singh, Rodeo; Jack H. Nunberg, Oakland, both of Calif.; Thomas R. Tice, Birmingham, Ala.; Michael E. Hudson, Gardendale, Ala.; Richard M. Gilley, Mountain Brook, AL; Terrance A. Taforo, San Leandro, Calif.

[73] Assignee: Cetus Corporation, Emeryville, Calif.

[21] Appl. No.: 231,757

[22] Filed: Aug. 12, 1988

Related U.S. Application Data

[63] Continuation-in-part of Ser. No. 856,680, Apr. 25, 1986, Pat. No. 4,818,769, which is a continuation-in-part of Ser. No. 778,371, Sep. 20, 1985, abandoned.

[51] Int. Cl.$^5$ ............................................. A61K 37/02
[52] U.S. Cl. ............................... 514/21; 514/2; 514/963; 514/921; 514/872; 514/12; 930/141; 424/499
[58] Field of Search ................... 514/12, 2, 921, 872, 514/963; 424/499; 930/141

[56] References Cited

U.S. PATENT DOCUMENTS

| | | | |
|---|---|---|---|
| 4,518,584 | 5/1985 | Mark et al. | 424/85 |
| 4,526,938 | 7/1985 | Churchill | 525/27 |
| 4,571,336 | 2/1986 | Houck et al. | 424/490 |
| 4,604,377 | 8/1986 | Fernandes et al. | 530/351 |
| 4,675,189 | 6/1987 | Kent et al. | 424/490 |
| 4,766,106 | 8/1988 | Katre et al. | 530/351 |
| 4,818,769 | 4/1989 | Nunberg | 514/2 |

FOREIGN PATENT DOCUMENTS

| | | |
|---|---|---|
| 0089062 | 9/1983 | European Pat. Off. . |
| 0092918 | 11/1983 | European Pat. Off. . |
| 0058481 | 10/1986 | European Pat. Off. . |
| 0248531 | 12/1987 | European Pat. Off. . |
| 0251476 | 1/1988 | European Pat. Off. . |

OTHER PUBLICATIONS

Beck et al., 1983, "Long-Acting Steroid Contraception" Raven Press, NY.
Beck et al., 1985, *Adv. Contracept.* 1:119–129.
Cowsar et al., 1985, *Methods in Enzymology* 112:101–116.
Reed et al., 1984, *J. Immunology* 133:3333–3337.
Hora et al., *Bio/Technology*, 8, 755–758 (1990).
Hora et al., *Pharmaceutical Research*, 7(11), 1190–1194 (1990).
Hora et al., *Pacific Polymer Conference*, 1, 519–520 (1989).

*Primary Examiner*—Ronald W. Griffin
*Attorney, Agent, or Firm*—Philip L. McGarrigle; Lewis S. Gruber; Grant Green

[57] ABSTRACT

Shipping fever, and other stress-related diseases in livestock, are treated by administration of a microencapsulated composition comprising IL-2 conjugated with a polyoxyethylene polymer, and mixed with a release-modulating amount of humen serum albumin. The microcapsules are administered parenterally, and release an effective amount of conjugated IL-2 continuously over a period of 14–30 days. These microcapsules are also effective in the treatment of cancer in mammals.

6 Claims, 23 Drawing Sheets

```
                    5                  10                 15                  20
AlaProThrSerSer SerThrLysLysThr GlnLeuGlnLeuGlu HisLeuLeuLeuAsp
            25                 30                 35                  40
LeuGlnMetIleLeu AsnGlyIleAsnAsn TyrLysAsnProLys LeuThrArgMetLeu
            45                 50                 55                  60
ThrPheLysPheTyr MetProLysLysAla ThrGluLeuLysHis LeuGlnCysLeuGlu
            65                 70                 75                  80
GluGluLeuLysPro LeuGluGluValLeu AsnLeuAlaGlnSer LysAsnPheHisLeu
            85                 90                 95                 100
ArgProArgAspLeu IleSerAsnIleAsn ValIleValLeuGlu LeuLysGlySerGlu
           105                110                115                 120
ThrThrPheMetCys GluTyrAlaAspGlu ThrAlaThrIleVal GluPheLeuAsnArg
           125                130                135                 140
TrpIleThrPheCys GlnSerIleIleSer ThrLeuThr---
```

FIG. 1

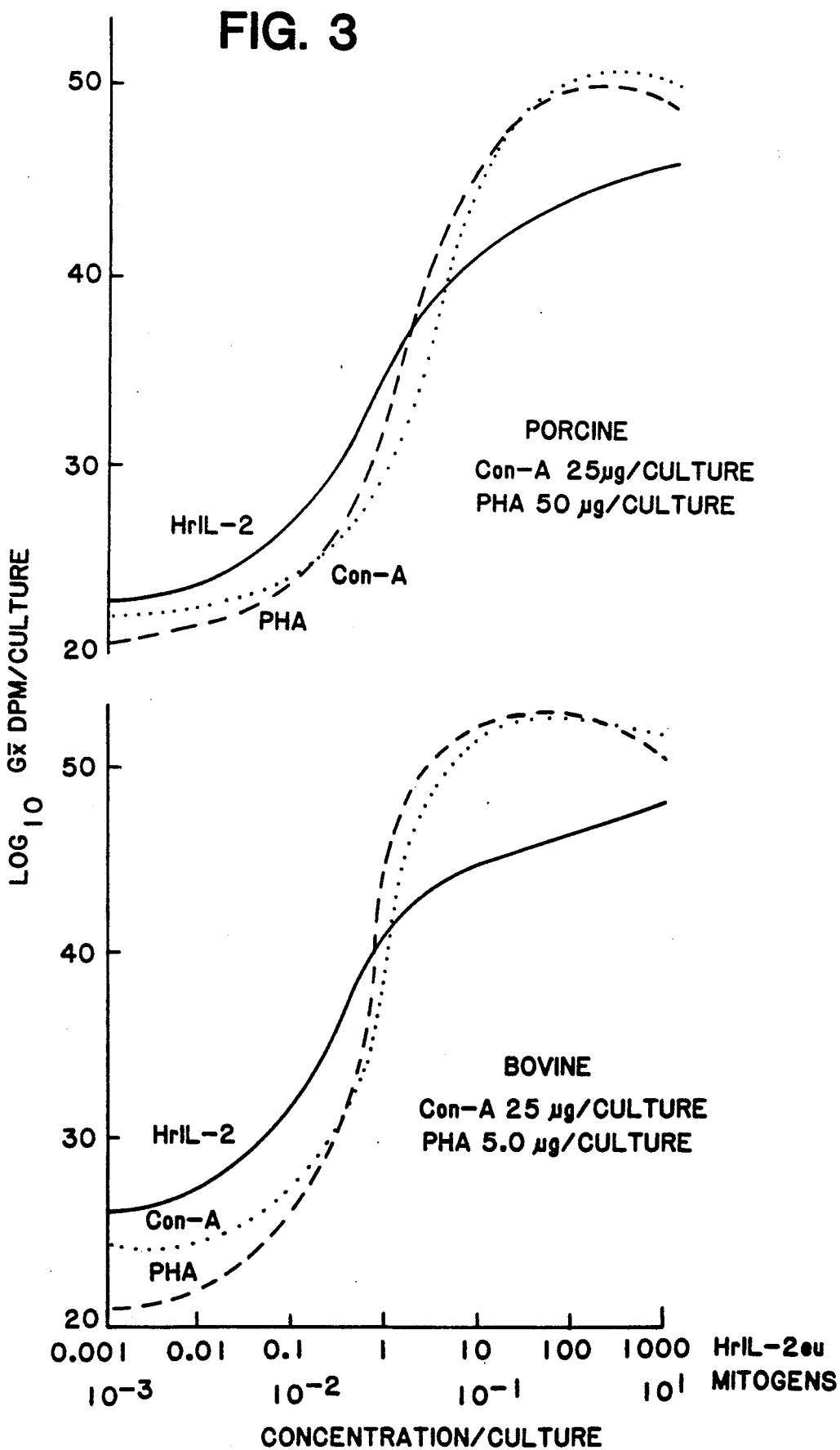

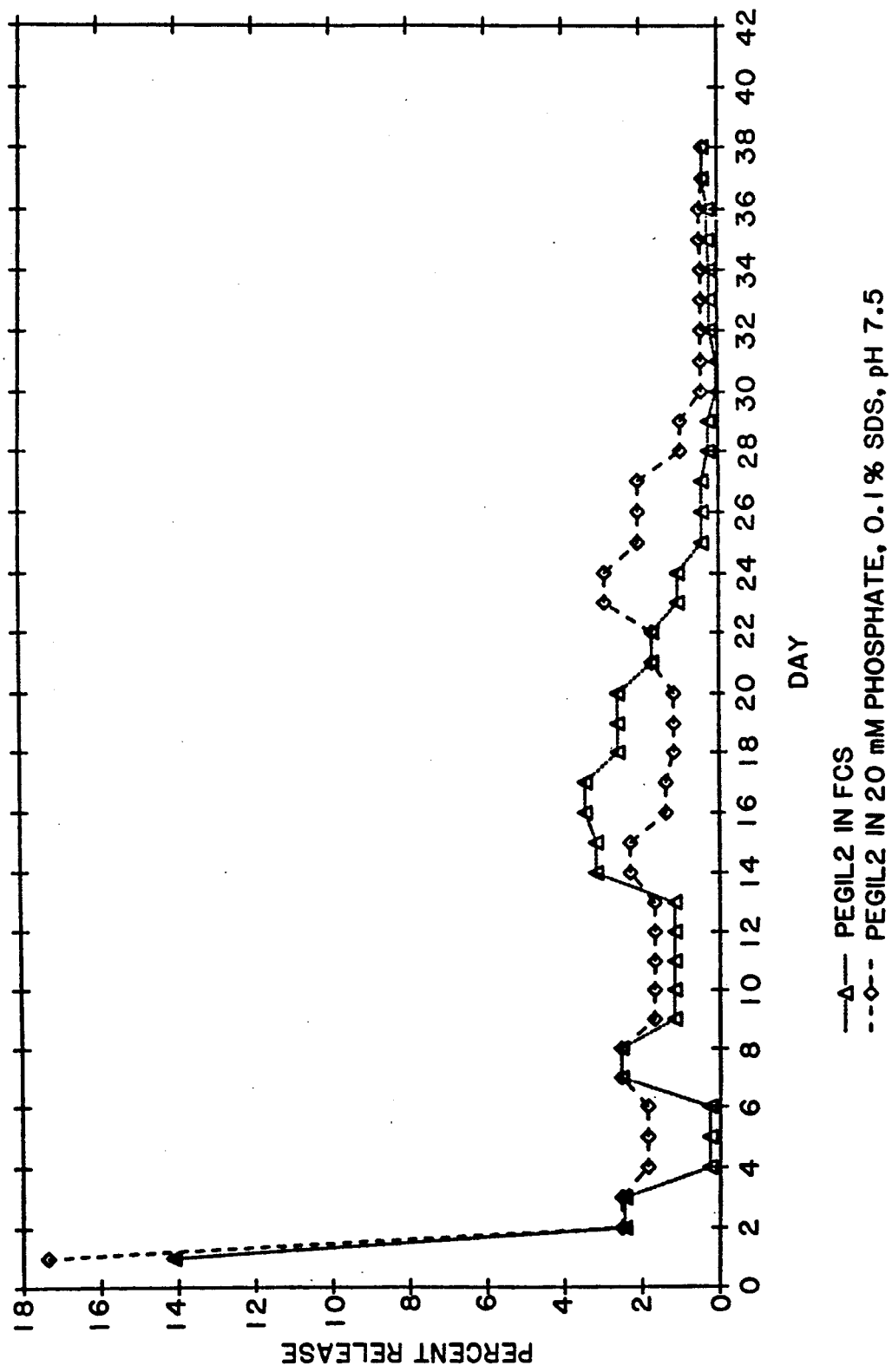

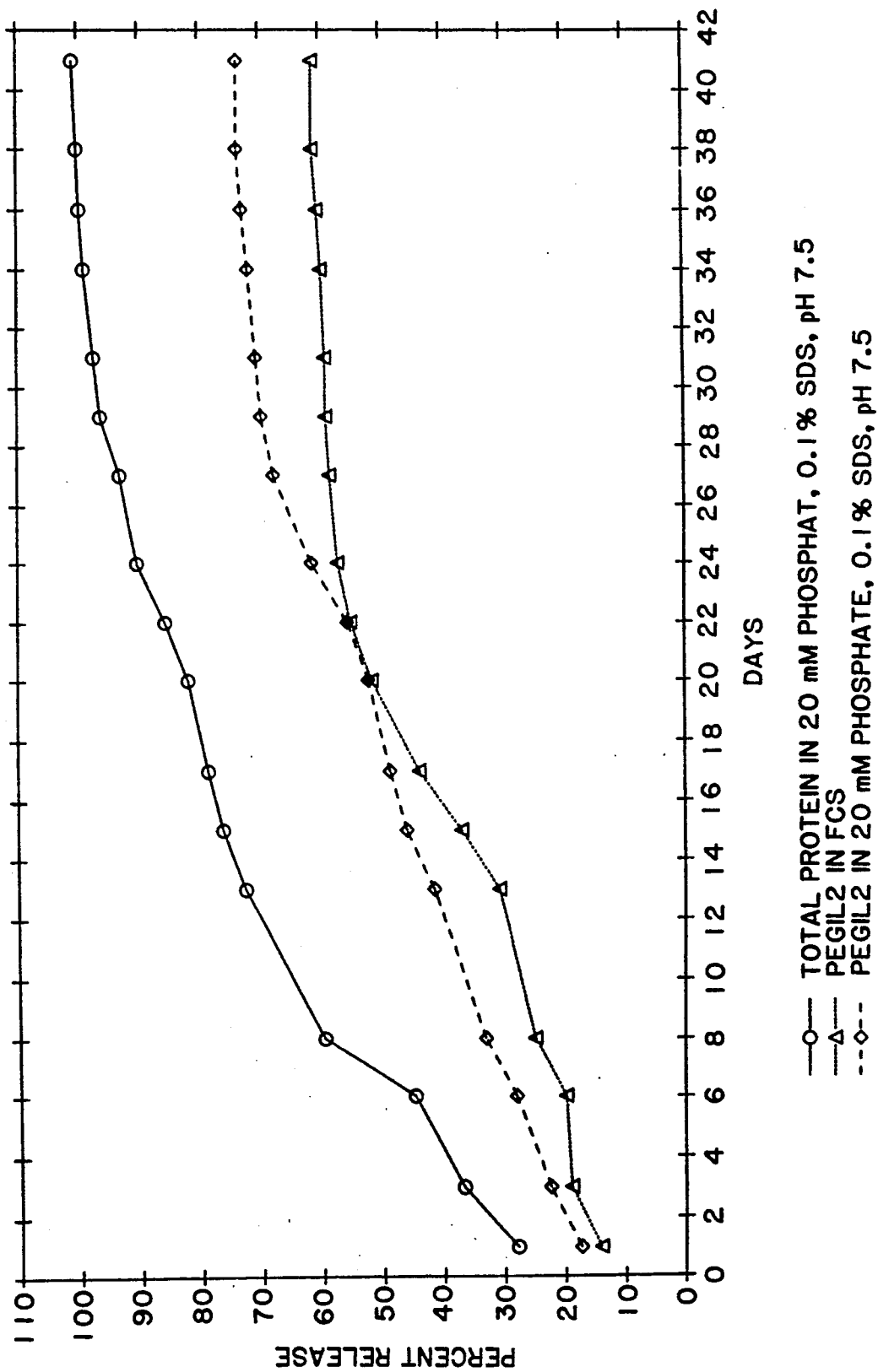

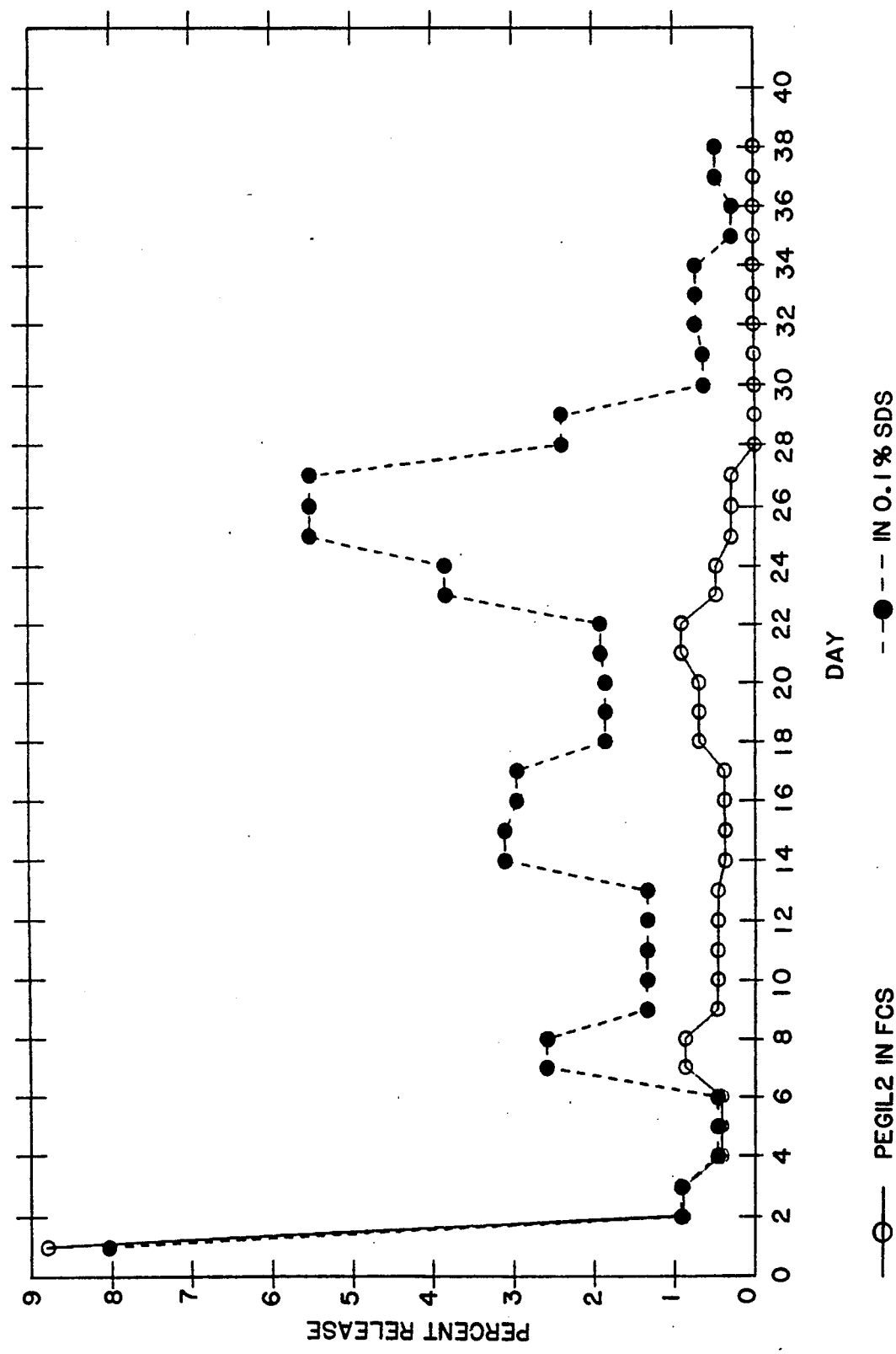

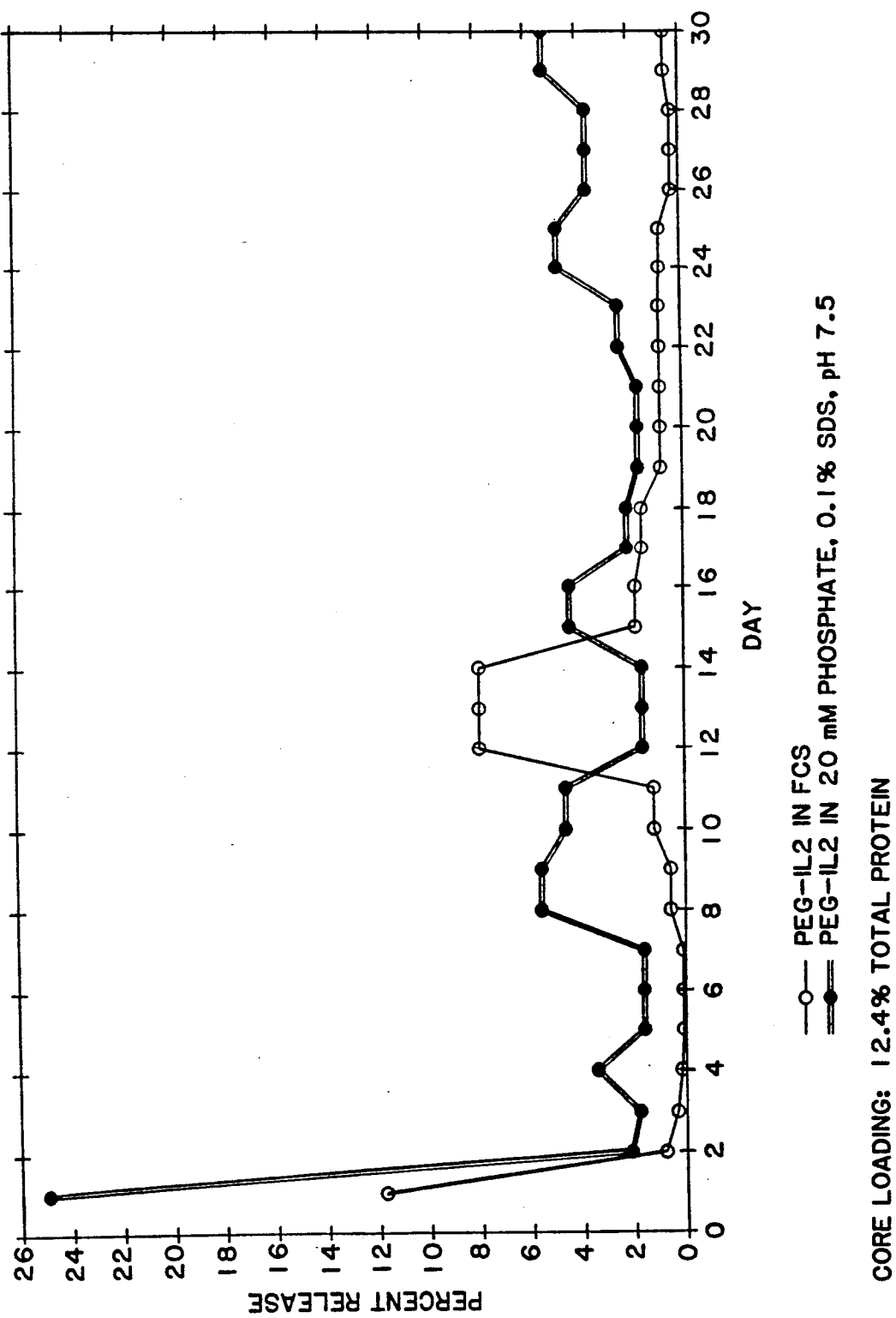

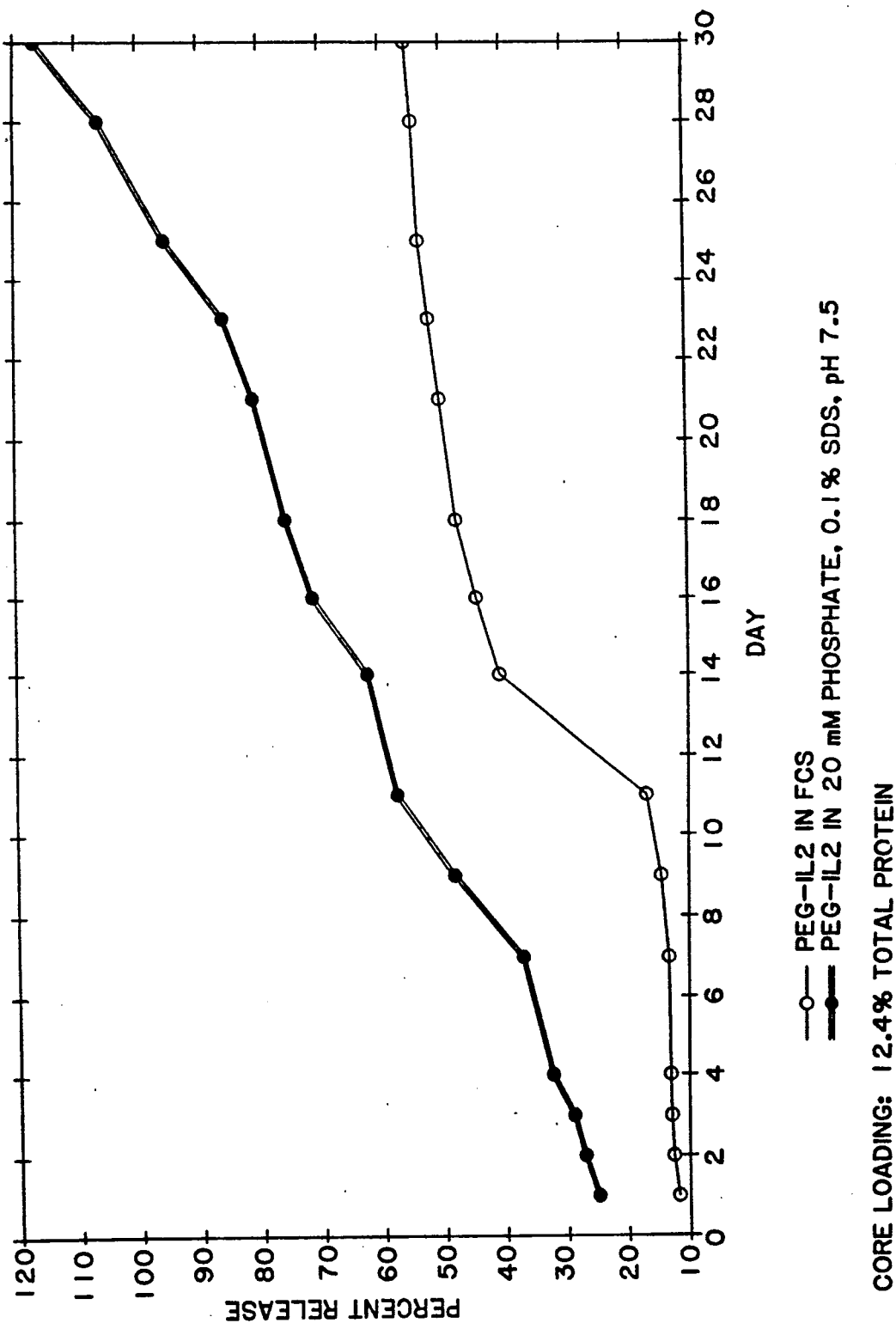

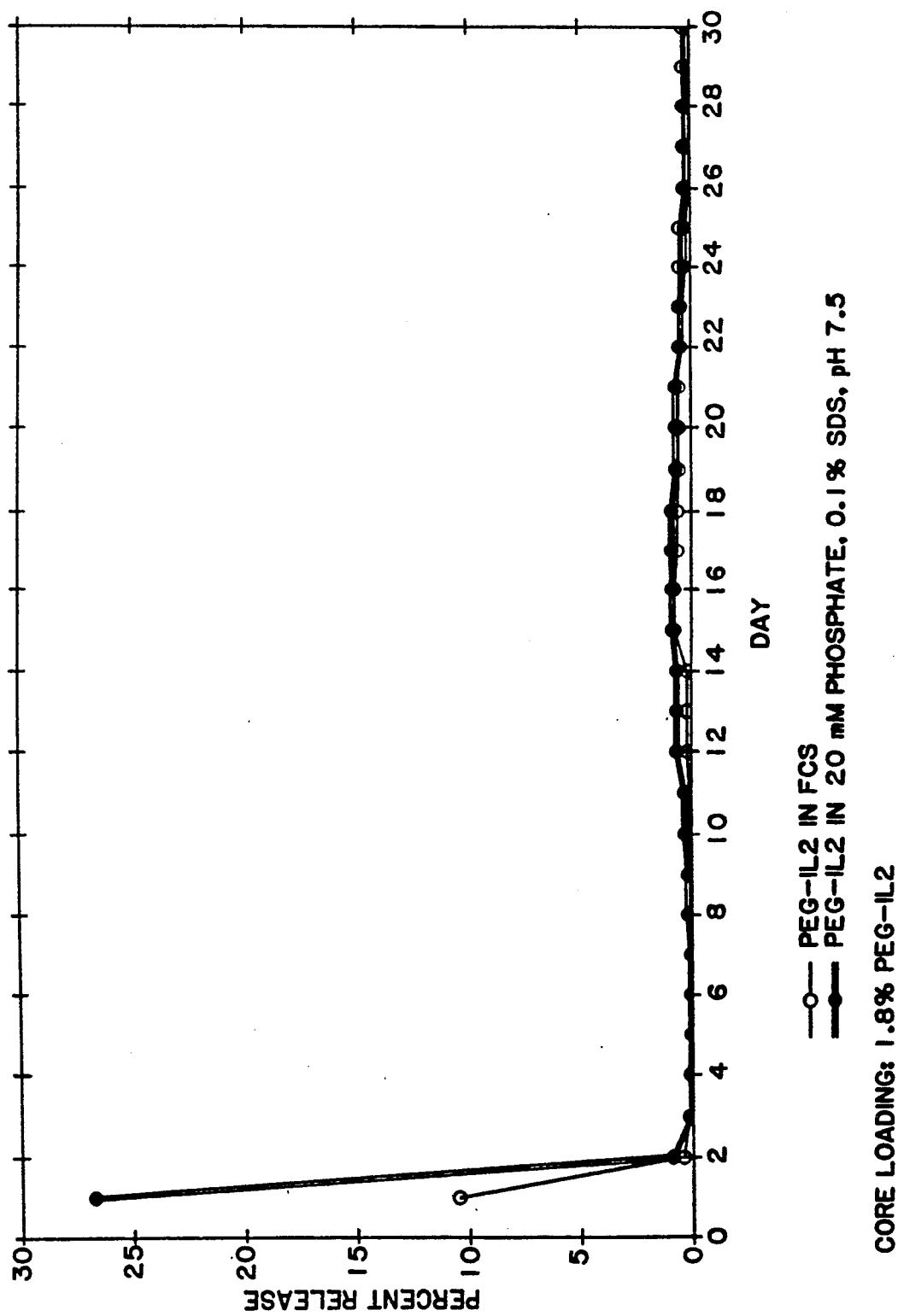

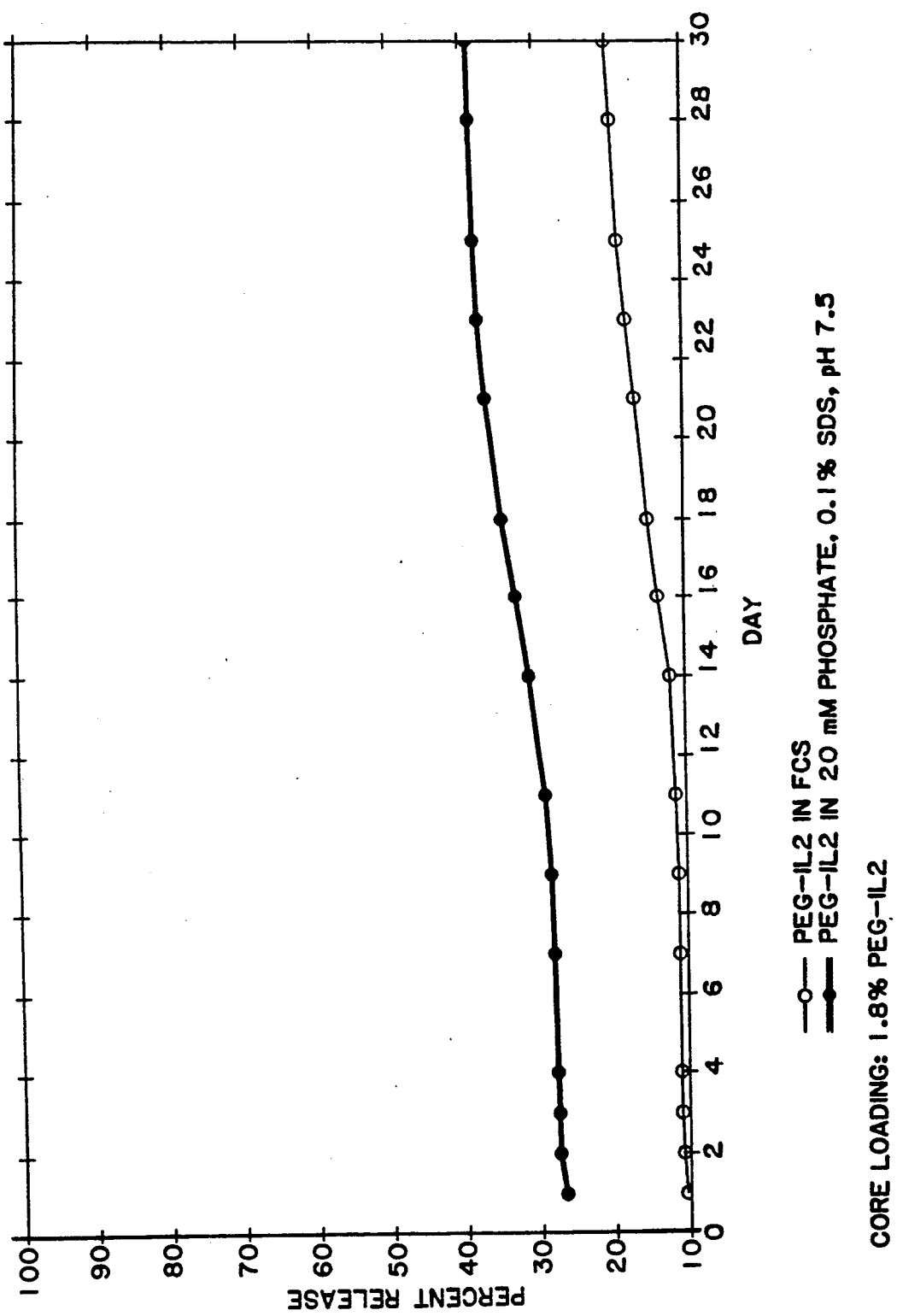

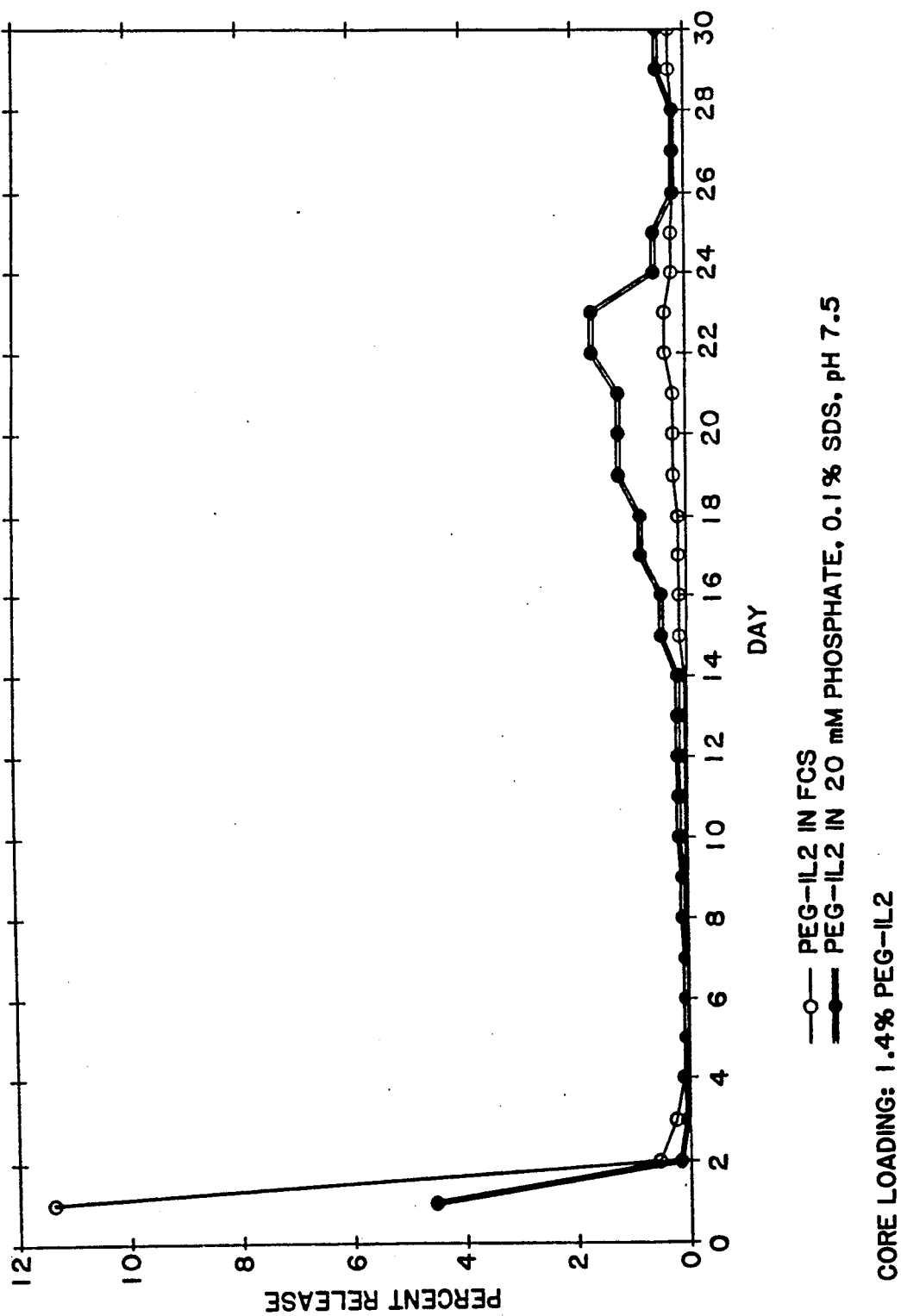

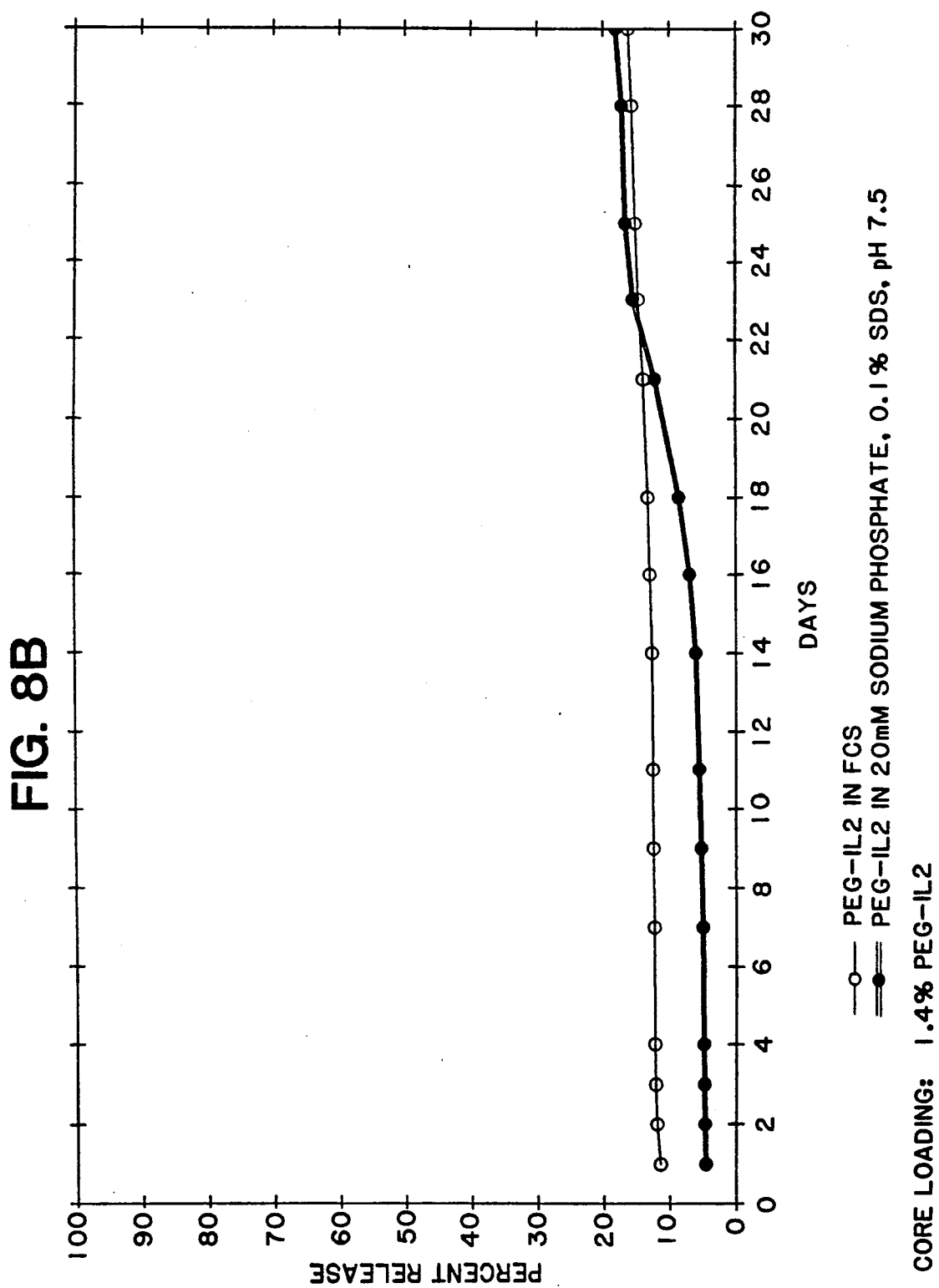

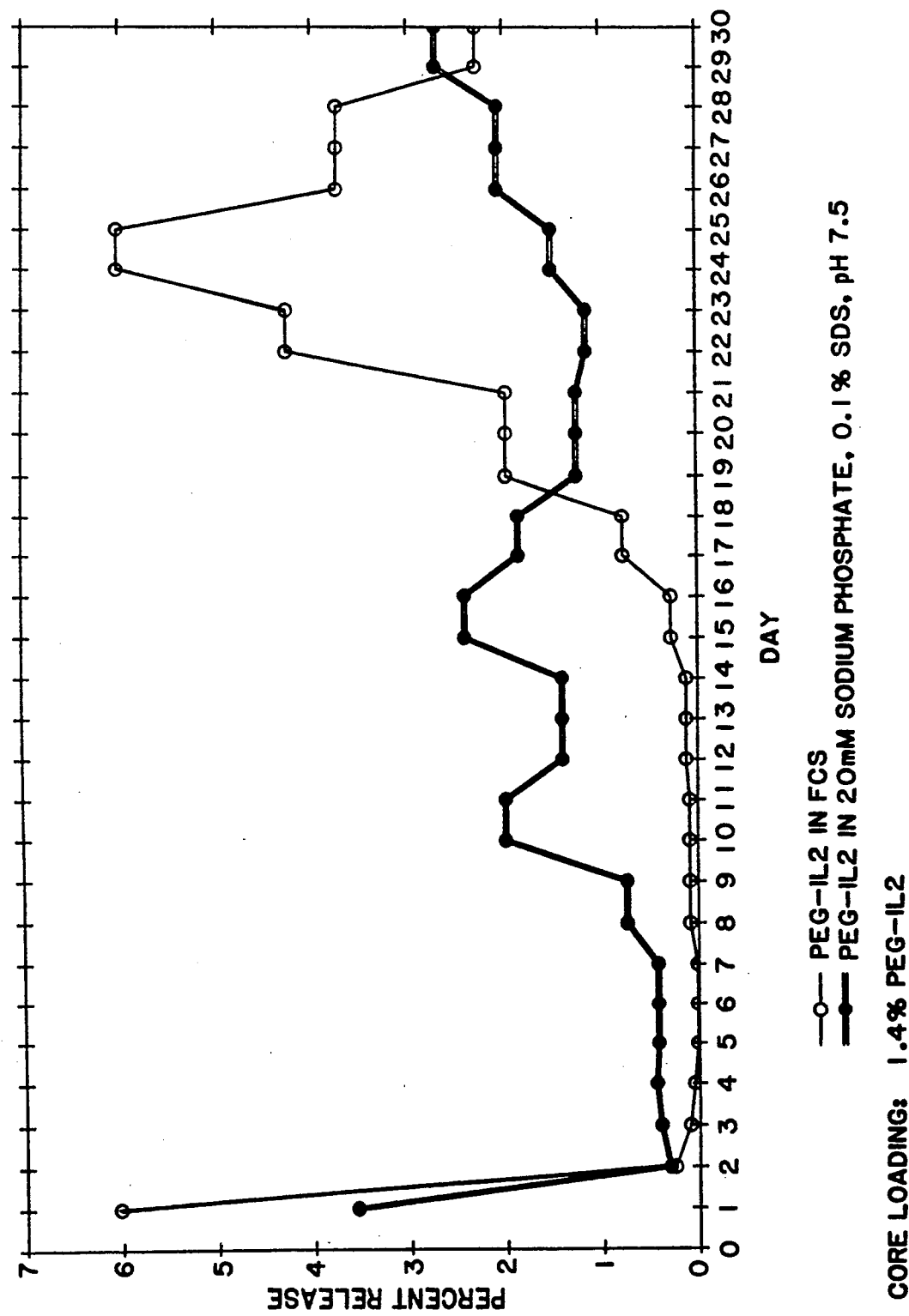

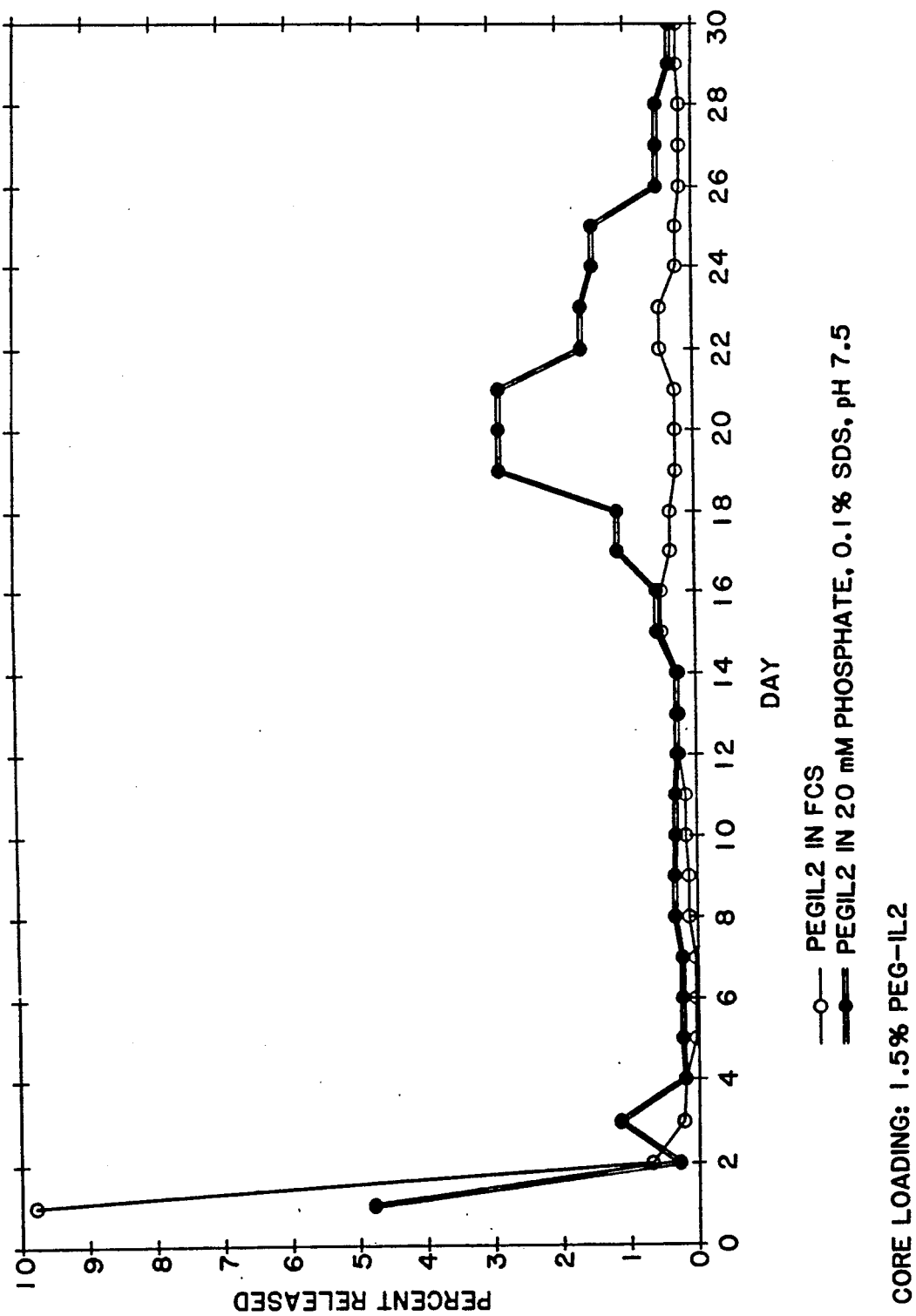

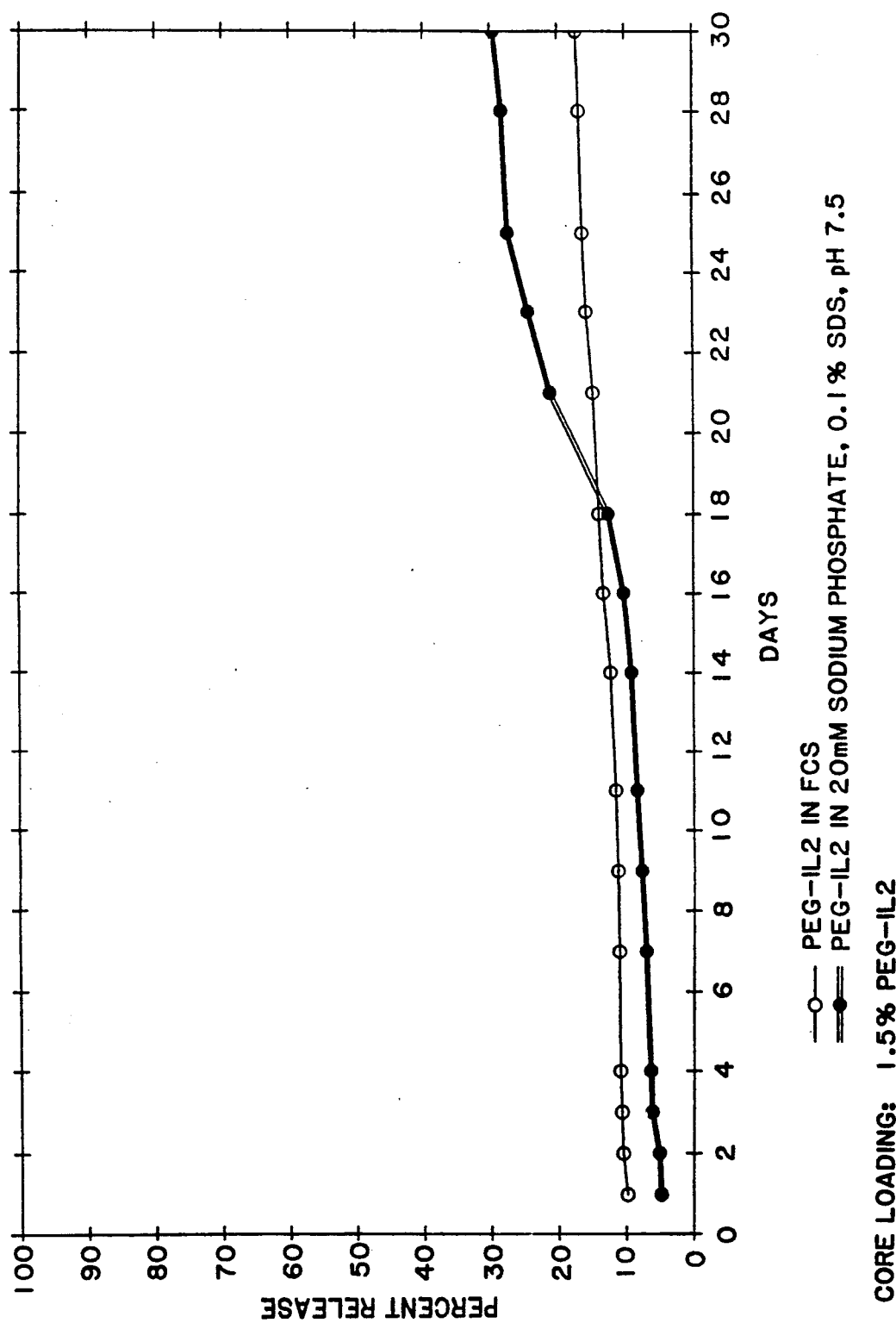

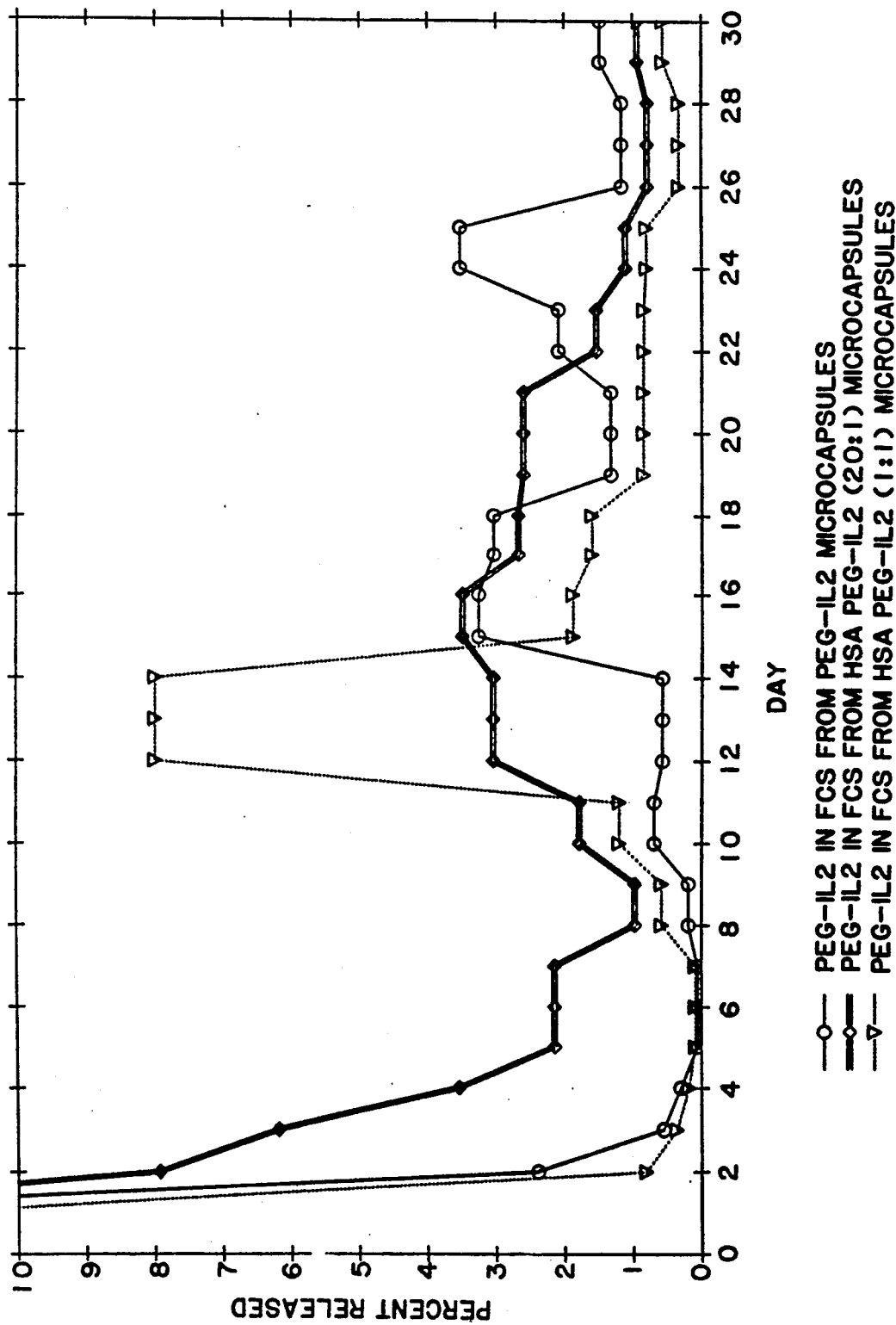

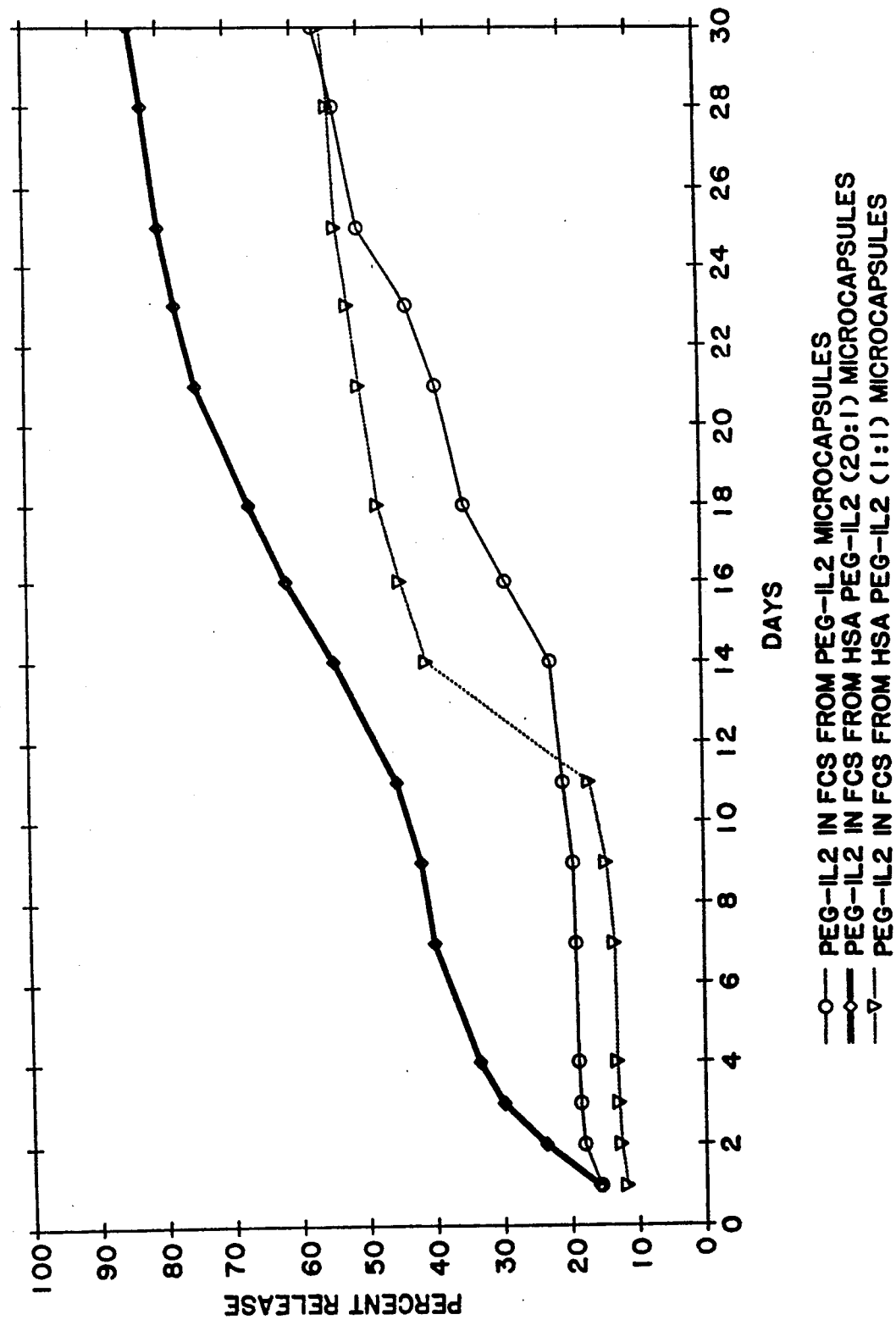

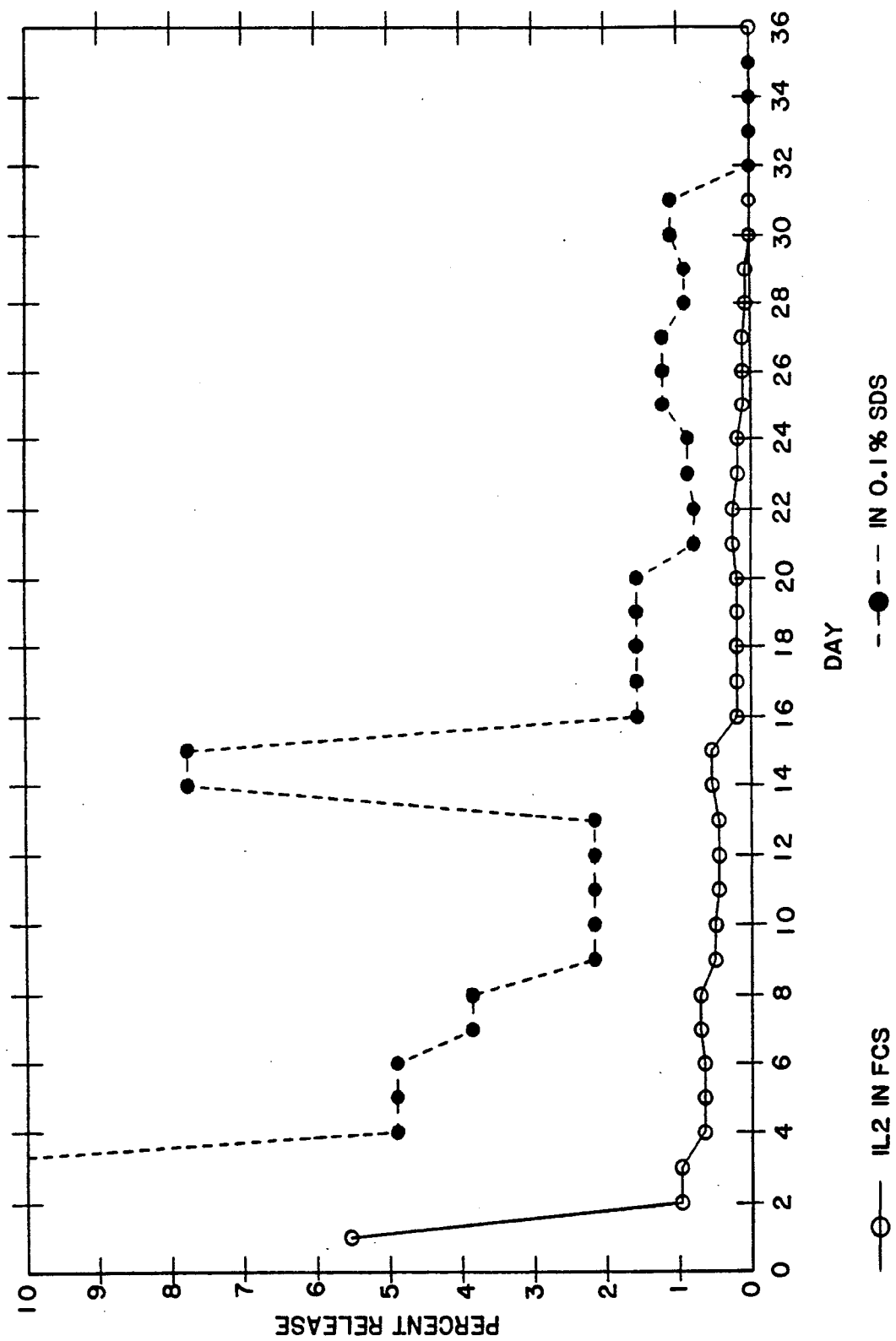

CONTROLLED-RELEASE FORMULATIONS OF INTERLEUKIN-2

RELATED APPLICATIONS

This application is a continuation-in-part of copending U.S. Application Ser. No. 856,680, filed 25 Apr. 1986, (incorporated herein by reference), now U.S. Pat. No. 4,818,769, which is a continuation-in-part of U.S. Application Ser. No. 778,371, filed 20 Sept. 1985, now abandoned.

BACKGROUND OF THE INVENTION

This invention is in the general fields of biochemical engineering and veterinary medicine. More specifically, this invention relates to improved, controlled-release formulations containing human interleukin-2 (hIL-2) and derivatives thereof for administration to livestock, and a method for preventing shipping fever and other stress-related diseases in livestock by administration of compositions of the invention.

Livestock food animals, particularly cattle, are adversely affected by shipment and feedlot conditions, which involve stress from overcrowding, weaning, transport, sometimes severe weather, etc.: in general, an unnatural environment. One syndrome, commonly known as "shipping fever" or bovine respiratory disease syndrome (BRDS) is a complex of diseases rather than a specific disease. BRDS is characterized by immune suppression and propensity to succumb to infection by one or more viral or bacterial pathogens.

Other animals also exhibit adverse reactions to stress. For example, pigs can suffer disease and/or negative respiratory reactions to weaning, or even poor weather. Again, the etiology does not lend itself to experimental modeling. No general treatment for stress-related disorders in livestock has been found. Sick animals are typically treated with antibiotics. Recently, interferon preparations have been offered for treating shipping fever.

There is considerable background information available with respect to the biological activity of hIL-2. IL-2 may be prepared by recombinant methods or obtained from appropriate cell cultures, e.g., from the supernatant of concanavalin-A (ConA) stimulated spleen cells. There are several activities measurable in vitro. First, IL-2 is a T-cell growth factor, as measured by thymidine uptake in cultures of cytotoxic or helper T-cell lines ($T_c$ or $T_h$) when IL-2 is added. It is mitogenic with respect to adult thymocytes, and stimulates a cytotoxic cell response in LAK (lymphokine-activated killer) cells. It has also been shown to replace $T_h$ cells in athymic murine spleen cell cultures (J. Watson et al, *Immunological Rev* (1980) 51:257-258). Specifically, in the presence of IL-2 and antigen, certain $T_h$ cells are stimulated which then are able to contribute to antibody responses. Presumably this occurs because IL-2 is involved in the antigen-dependent maturation of $T_h$ cells in these nude mouse spleen cultures.

IL-2 has also been shown to directly affect B cells in vitro. Both B cell proliferation and antibody secretion (IgM and IgG) are enhanced by IL-2 in populations of purified, activated B cells (M.C. Mingari et al, *Nature* (1984) 312:641; R. Mittler et al, *J Immunol* (1985) 134:2393-2399; A. Muraguchi et al, *J Exp Med* (1985) 161:181-197).

It is not clear how these in vitro activities translate into a specific in vivo mechanism for mounting an immune defense. However, with respect to in vitro studies, cross-reactivity among species of various IL-2s has been studied. For example, hIL-2 supports activated rabbit and mouse T lymphocytes to approximately the same extent as the endogenous rabbit or mouse IL-2 (D. Redelman et al, *J Immunol Method* (1983) 56:359-370). Human IL-2 behaves as a growth factor not only for human T-cells, but also peripheral blood lymphocytes or splenocytes from other primates, horse, guinea pig, cat, rat, and mouse (F.W. Ruscetti et al, *Blood* (1981) 57:379-393). Human IL-2 is also known to enhance the development and maintenance of bovine cytotoxic lymphocytes in *vitro* (J. Carter et al, *Fed Proc* (1985) 44:1290). Native hIL-2 and recombinant IL-2 exhibit the same range of activity on animal cells in in vitro lymphocyte proliferation studies (M.V. Doyle et al, *J Bio Resp Mod* (1985) 4:96-109).

Some in vivo data are also available. The administration of IL-2 in vivo has been shown to restore immunocompetence in nude mice in response to heterologous erythrocytes (H. Stotter et al, *Eur J Immunol* (1980) 10:719-722). There is some information concerning in vivo cross-species reactivity as well. Human IL-2 is able to reconstitute spleen cell responses in mice infected with a parasitic protozoan (S.G. Reed et al, *J Immunol* (1984) 133:3333), while in vivo injection of IL-2 of human origin stimulates the splenic T-cells in nude mice (J.J. Farrar et al, *Immunol Rev* (1982) 63:158).

In summary, it is known that IL-2 behaves in some manner in vivo to mediate a successful immune response, including a response to a specific antigen, and in vitro studies have shown that cross-species reactivity of hIL-2 is very diverse (prior in vivo cross-species studies have involved only murine subjects for hIL-2). However, because the mechanism of involvement of IL-2 in the immune response is not understood, it is not possible to predict the behavior of IL-2 in boosting an immune response to prevent or ameliorate a particular disease or to predict its overall effect. Accordingly, there is no suggestion in the art that IL-2, and in particular hIL-2, would successfully mitigate the incidence of shipping fever or other stress-related syndromes that affect livestock.

Additionally, administration of protein and polypeptide agents to livestock has proved to be quite problematic. As peptides and proteins are typically digested upon oral administration, such agents must be administered by parenteral means. Many biologically active peptides and proteins have extremely short halflives in serum, which necessitates frequent administration (e.g., b.i.d.) to maintain therapeutic levels of the drug. Although this is an acceptable administration regime for human subjects (although not necessarily preferred), it may be considered unacceptable to the rancher who must treat hundreds or thousands of animals. The business of growing livestock is highly competitive, and lends a keen sense of economy to the operator. Thus, any treatment program must provide a tangible benefit, for example, increased weight gain in animals, increased lean to fat ratio, increased survival rate, etc. Further, the benefits must outweigh the cost of treatment, including the cost of personnel to administer the treatment. As excessive handling is detrimental to livestock (intramuscular injection while an animal is restrained in a chute is quite stressful to the subject), these goals are best met by selecting an active agent which is inexpensive and administered only infrequently (preferably only once). Infrequent administration is also preferred for the reason that it minimizes the chance of infection, as such administration is typically not performed in an ideal, hygienic environment.

Accordingly, a peptide or protein agent should either have a long half-life in the serum, or should be administered using some form of controlled release device. Such devices as used for other veterinary agents are typically either membrane-type devices (having a central reservoir containing the active compound, surrounded by a rate-controlling membrane), or monolithic-type devices (typically a solid matrix, e.g., of silicone rubber, having the active compound dispersed throughout). Design of such devices must balance the factors of release rate, completeness of delivery, and induction period, as well as biocompatibility and acceptability for use in food animals.

The ideal controlled-release device would administer the active compound at a constant ("zero-order"), therapeutic rate, beginning at the moment of administration and continuing until 100% of the compound contained in the device had been released. Further, the device would not cause inflammation or other adverse effects, and would leave no residue. Frequently, such devices as are presently used (e.g., Compudose ®, a silicone rubber matrix impregnated with growth-promoting steroids) are administered to portions of the animal not used for food, e.g., in the ear cartilage, or in portions of the animal removed at slaughter as offal.

However, the characteristics of the ideal device are seldom attained. The release pattern of most devices consists of a high initial release rate, followed by a logarithmically declining release falling eventually to subtherapeutic levels. Typically as much as 20-40% of the active compound is retained in the implant and is never released. Caution must be exercised that the initial release does not provide toxic serum levels of the active compound. The amount of compound released in excess of the therapeutic level, and that which is retained in the device, is essentially wasted. This is a particularly egregious drawback when the active compound is an expensive peptide or protein agent. Further, even when the device is not especially inflammatory, a foreign-body reaction often ensues which results in the device's encapsulation in fibrous tissue. Such encapsulation impedes the drug administration, and degrades the quality of meat at the injection site.

One form of sustained-release delivery system is the microcapsule or microsphere. Microcapsules/spheres are essentially small particles of active compound embedded in a suitable polymer to form spheres ranging in diameter from about 40-500 um. Microcapsules of less than about 300 um (preferably <150 um) are easily administered by injection when suspended in a suitable liquid vehicle. A large variety of polymers may be selected for use in microcapsules, although the particular polymer which is best suited for a particular application is often difficult to determine. The necessary considerations include interaction between the polymer and the active compound, the solubility of the compound in the polymer, the stability of the polymer and its rate of degradation (if any), its biocompatibility, the morphology of the resulting microcapsule as it degrades, etc. Microcapsule formulations encapsulating steroids and other agents are reported in the literature, for example, T.R. Tice et al, *Pharm Tech* (1984) 8:26-35; D.R. Cowsar et al, *Meth Enzymol* (1985) 112:101-116; and L.R. Beck et al, "Long Acting Steroid Contraception" (1983, Raven Press, NY, Ed. D. Mishell) pp. 175-199.

DISCLOSURE OF THE INVENTION

The invention provides a practical approach to controlling a poorly defined disease that affects an estimated 12 million cattle per year in the United States alone, resulting in a half million deaths among young cattle with the concomitant waste in food supplies. The symptomatology associated with shipping and feedlot cultivation of these cattle can be controlled using hIL-2, including the recombinant forms thereof. In addition, all livestock suffer from characteristic adverse, infection-related reactions to stress, and exhibit poorly defined symptomatologies which are similarly treatable. By utilizing the available recombinant forms, a supply of effective hIL-2 is made available in practical amounts and at relatively low cost.

In one aspect, the invention relates to methods of controlling (i.e., prophylaxis or amelioration of severity or duration) shipping fever or other adverse reactions to stress in livestock by administration of an effective dose of hIL-2 or IL-2 equivalent, including that recombinantly produced, in the particularly effective microcapsule formulation of the invention.

In other aspects, the invention relates to symptomatolytic formulations of hIL-2 for controlling such stress-related symptoms. Such formulations comprise PEGyl-IL-2 combined with a release-modulating amount of HSA and microencapsulated in a biocompatible, bioerodible poly(lactide-co-glycolide) excipient. We have found that the controlled-release formulations of the current invention, by delivering a relatively constant, effective amount of IL-2, overcome the problems of IL-2's short serum half-life. Thus, the formulations of the invention are suitable for treatment of any disease or disorder which responds to treatment with IL-2 in more conventional formulations. By employing the controlled release formulation of the invention, however, the therapeutic regime is improved from daily injections to one injection every two weeks or more.

In another aspect, the microcapsule formulations of the invention are used in the prevention and/or treatment of cancer and related neoplastic disorders in mammals.

BRIEF DESCRIPTION OF THE DRAWINGS

FIG. 1 shows the amino acid sequence of native hIL-2.

FIG. 3 shows the effect of hIL-2 on blastogenesis of bovine and porcine T-lymphocytes, as described in Example 1.

FIGS. 4A, 4B, 4C, 4D, 5A, 5B, 6A, 6b, 7A, 7B, 8A, 8B, 9A, 9B, 10A, 10B, 11A, 11B, 12A and 12B show the in vitro release of IL-2 from microencapsulated formulations, as described in Example 5.

Modes of Carrying Out the Invention

A. Definitions

Figure 2A:
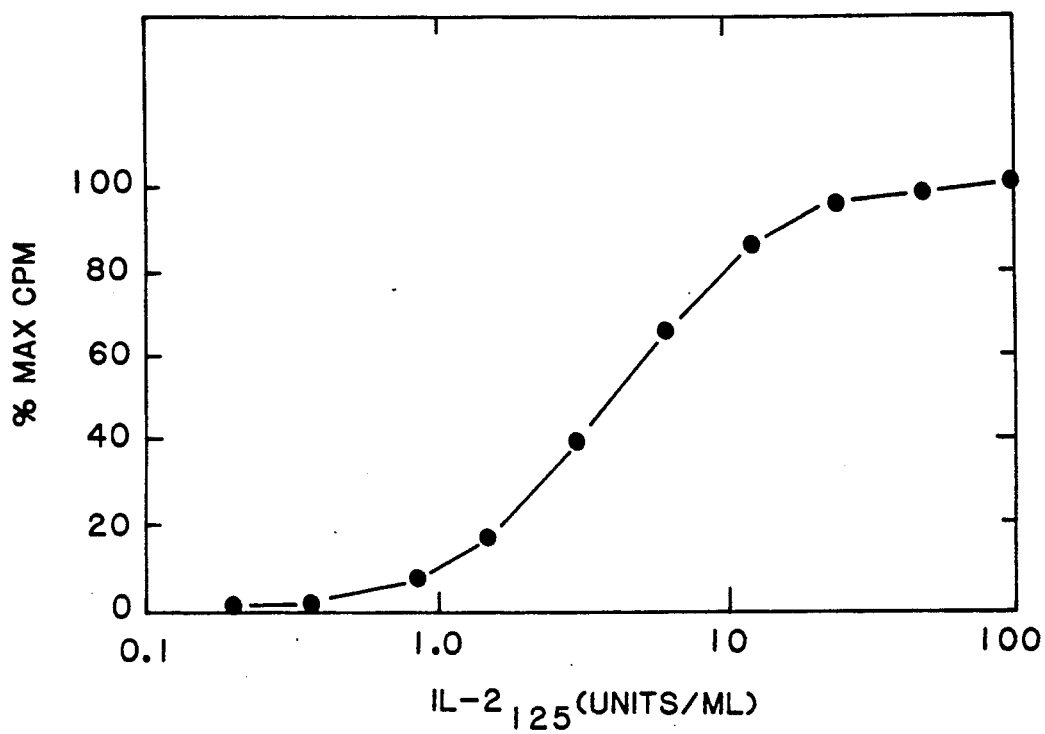
FIGS. 2A and 2B are dose-response curves showing the results of the lymphocyte proliferation tests described in Example 1.

As used herein, "hIL-2" refers to a protein exhibiting the spectrum of activities characterizing human interleukin-2. Specifically, the protein must be capable of stimulating the proliferation of hIL-2 dependent cytolytic and helper T cell lines, as set forth in the standard assays of S. Gillis et al, *J Immunol* (1978) 120:2027–2032 and of J. Watson, *J Exp Med* (1979) 150:1510–1519. The amino acid sequence of native hIL-2 is shown in FIG. 1. The protein of this primary amino acid sequence may be obtained by purification from natural sources or may be recombinantly derived. Other primary sequences of modest modification, including deletion, addition, substitution or alterations of the amino acids of the sequence shown, which do not result in serious impairment of activity are also included in this definition. For example, it is established that replacement of the cysteine at position 125 with a neutral amino acid results in a mutein of superior stability and satisfactory activity. (See U.S. Pat. No. 4,518,584; M.V. Doyle et al, supra). In addition, IL-2, like any other protein, may exist in neutral or in salt form, and may have bound non-peptide modifications resulting from in vivo or in vitro glycosylation, phosphorylation, or acetylation. Proteins so modified are also included in this definition so long as biological activity is not destroyed thereby.

A variety of techniques may be used to effect long-term stability. For example, stability is enhanced by coupling to a homopolymer such as polyethylene glycol (PEG), as described in copending commonly owned U.S. patent application Ser. No. 749,955, filed 26 June 1985, now abandoned, incorporated herein by reference. This PEGyl-hIL-2 derivative, sometimes called "PEGylated" hIL-2, is particularly useful for administering a single sustained action dose of hIL-2. IL-2 which has been modified by any of the above methods, for example by site-specific mutagenesis or by conjugation with polymers, is referred to herein as IL-2, or as an "IL-2 equivalent."

The term "PEGyl-IL-2" refers to an IL-2 protein conjugated to a polyol polymer, for example polyoxyethylene, methyl polyoxyethylene, polyoxyethylene -polyoxypropylene block polymers, polyoxyethylated glycerol ("POG"), polyoxyethylated sorbitol, polyoxyethylated glucose, and the like. The polyol molecular weight is not critical, but should impart or increase water solubility to the IL-2 protein when attached. Thus, the polyol selected will preferably have a molecular weight between about 300 and 100,000 daltons, more preferably between about 4,000 and 40,000 daltons. The IL-2 protein may be a native IL-2 derived from any mammalian species, preferably human, bovine, or porcine, or may be a recombinantly produced IL-2 or IL-2 mutein exhibiting at least 20% of native IL-2 activity. Presently preferred IL-2 proteins are native hIL-2, and the hIL-2 muteins des-ala$_1$IL-2, des-ala$_1$-ala$_{104}$IL-2, cys$_3$ser$_{125}$IL-2, des-ala$_1$cys$_3$ser$_{125}$IL-2, cys$_3$ala$_{125}$IL-2, des-ala$_1$cys$_3$ala$_{125}$IL-2, cys$_3$ala$_{104}$-IL-2, des-ala$_1$cys$_3$ala$_{104}$IL-2, cys$_3$ala$_{104}$ser$_{125}$IL-2, cys$_3$ala$_{104}$ala$_{123}$IL-2, des-ala$_1$cys$_3$ala$_{104}$ala$_{125}$IL-2, and des-ala$_1$cys$_3$ala$_{104}$ser$_{125}$IL-2. Preparation of hIL-2 and the preferred muteins is described in copending U.S. Pat. Application No. 810,656, filed 17 Dec. 1985, now abandoned, incorporated herein by reference.

The term "HSA" refers to human serum albumin. HSA is preferably used in the practice of the instant invention to stabilize and modulate PEGyl-IL-2 release from PLG microcapsules, although it should be understood that serum albumins from other mammalian species (e.g., bovine serum albumin—BSA) are considered equivalents within the scope of this invention. HSA is a staple of commerce. A "release modulating amount" of HSA is that amount which when mixed with PEG-IL-2 and encapsulated in poly(lactideco-glycolide) microspheres ensures the desirable release characteristics of the invention. The precise quantity of HSA will vary depending upon the exact form of HSA (or equivalent), IL-2, and polymer, but will generally be within the ratio range of about 1:5 to about 1:30 IL-2:HSA by weight.

The term "PLG" refers to poly(lactide-co-glycolide), a biodegradable polymer known in the art. PLG may be prepared by ring-opening polymerization of freshly prepared dimers of d,l-lactic acid (or l-lactic acid) and glycolic acid at 160° C., using organotin compounds as catalysts. The molecular weight may be controlled using chain-transfer agents such as d,l-lactic acid. Where desired, the molecular weight of a given sample may be reduced by autoclaving the polymer at, e.g., 121° C. under 15 psig steam pressure. The molecular weight may be determined using gel-permeation chromatography, with polystyrene standards, or by viscometric methods. PLG is a random copolymer, and need not contain lactide and glycolide in equimolar amounts. The polymer's solubility and degradation characteristics may be adjusted and optimized by varying the relative ratios of lactide and glycolide in the polymer. PLG and its preparation and use to prepare microcapsules is described in T.R. Tice et al, *Pharm Tech* (1984) 8:26–35; D.R. Cowsar et al, *Meth Enzymol* (1985) 112:101–116 and L.R. Beck et al, "Long-Acting Steroid Contraception" (1983, Raven Press, NY, Ed. D. Mishell) pp. 175–199.

The terms "microspheres" and "microcapsules" are used interchangeably herein, and refer to polymer particles having IL-2 or PEGyl-IL-2 contained or dispersed within. As a result of the method of manufacture, microcapsules will not have a precise, uniform diameter, but will generally be provided as a population having diameters ranging from about 10 to about 400 um. The process employed in the instant invention produces microspheres having an average diameter of about 100 um, and ranging from about 70 to about 140 um. PLG microcapsules are biodegradable, and thus provide a three-component release profile. The first phase ("initial burst") releases loosely bound and non-encapsulated compound (this may be eliminated, if desired, by washing the microcapsules prior to use). In the second phase, compound diffuses through the PLG, or through pores in the PLG, which appear and enlarge as degradation of the polymer progresses. In the third phase, compound which has been trapped within the polymer matrix, unable to diffuse, is released by the final breakdown of the polymer. The timing of these phases is adjusted by varying the size and solubility of the active compound in the polymer, (e.g., by using more or less soluble forms, including cosolvents, etc.), washing the loaded microcapsules to remove unbound active compound, adjusting the molecular weight and density of the polymer, varying the loading level (ratio of protein to polymer), adjusting the average microcapsule size, and the like.

The term "initial burst" refers to a characteristic of release curves, wherein administration is followed by an immediate, high release of compound (e.g., >8% of the total encapsulated protein). The initial burst is believed to be caused by the incomplete encapsulation of protein in microcapsules, or the degradation of microcapsules due to storage or handling. Thus, any non-encapsulated protein will be immediately present in solution. The initial burst may prove beneficial in some circumstances, e.g., by establishing a therapeutic plasma level of hIL-2 rapidly following administration. However, care must be exercised that the initial burst does not release a toxic level of hIL-2.

The term "induction period" refers to an undesirable characteristic of some release curves, wherein administration is followed by a period of at least 12 hours characterized by lack of compound release, or release at low (e.g., subtherapeutic) rates (e.g., <1%). The induction period may, but need not, follow an initial burst. It is highly desirable to minimize or eliminate the induction period.

As used herein the term "stress-induced syndrome" refers to a state of immunosuppression in which an animal has an increased susceptibility to infection by one or more bacterial or viral pathogens, loses weight, and/or exhibits general ill health and malaise.

"Shipping fever" or "bovine respiratory disease syndrome" (BRDS) is defined as negative symptomatology including depression, immunosuppression, weight loss, respiratory problems, viral or bacterial infection, and general ill health and death which are associated with the transportation of cattle to, and the maintenance of cattle on, feedlots. The disease is defined in terms of epidemiology rather than in terms of a model which describes the course of an infection or specific set of metabolic parameters.

However, certain parameters of the disease are recognized. It is characterized by an abrupt onset, usually within two weeks of stress, and the symptoms may include dyspnea, cough, ocular and nasal discharge, inappetance and rapid weight loss, fever, increased lung sounds, and general depression. Various bacterial and viral cultures have been isolated from affected animals, including Pasteurella spp, Haemophilus spp, infectious bovine rhinotracheitis, parainfluenza-3 virus, and bovine respiratory syncytial virus. The disease typically affects 40-50% of exposed animals and the resulting deaths are typically 2-5% of the exposed population. The criterion for effectiveness against this disease is the maintenance of healthy animals faced with the specific conditions associated with shipping stress and feedlot maintenance.

The term "cancer" as used herein includes disorders of cell proliferation and differentiation, commonly considered neoplastic or malignant. Cancer includes, for example, carcinomas, leukemias, myelomas, sarcomas, and the like.

The term "treatment" as used herein includes (1) prevention of symptoms and/or disease (prophylaxis), (2) inhibition of symptoms or disease, e.g., oncostasis, where symptoms do not worsen, and (3) cure, where disease symptoms are reduced or eliminated.

B. General Method

IL-2 is prepared by methods now known in the art. PEGyl-IL-2 is prepared by the methods described in commonly-owned U.S. Patent Application Ser. No. 749,955, filed 26 June 1985, now abandoned, incorporated herein by reference. HSA is commercially available in solution and as a lyophilized powder. PLG may be prepared as described in D.R. Cowsar et al, *Meth Enzymol* (1985) 112:101-116, incorporated herein by reference.

Appropriate amounts of PEGyl-IL-2 and HSA are combined either in solution or as finely divided powders. The PEGyl-IL-2+HSA composition is then microencapsulated in PLG. A solution of PLG in methylene chloride is stirred, and the PEGyl-IL-2+HSA composition dispersed therein. The protein composition is added in an amount sufficient to obtain microcapsules containing 1-20% protein, preferably about 8-17% protein by weight. We have found that higher loading levels tend to cause enhanced initial burst release, while lower loading levels correlate with unacceptably low release rate and/or induction periods. The mixture is homogenized to obtain a suspension, then poured into an aqueous solution of 6% poly(vinyl alcohol) and 2% $CH_2Cl_2$, stirring at 1000 rpm. After about 5 minutes, the suspension is poured into water and stirred at about 800 rpm for 15 minutes. The resulting microcapsule suspension is filtered over a 45 um sieve, washed with water, and dried at room temperature in vacuo for 48 hours. It will of course be appreciated by those of ordinary skill in the art that microcapsules may be prepared by a variety of methods, however, the above-described method provides particularly preferred microcapsules, having a narrow size distribution and high encapsulation efficiency. Other microcapsules within the scope of this invention will contain PEGyl-IL-2+HSA, (or an HSA equivalent), will be able to release the composition at a rate of about 2-5%/day with an induction period of <24 hours, and will not induce unacceptable toxicity in the subject animal.

The formulations of the invention are most conveniently administered by intramuscular injection, although other methods of administration are possible. Specific formulations to prevent hydrolysis during digestion would be necessitated for oral formulation, and intravenous injections are generally impractical due to the skill level and care required in the administration. Therefore, formulations suitable for subcutaneous, intramuscular, or intraperitoneal injection are preferred.

Formulations of the invention will generally be injectable suspensions of microcapsules, or dry microcapsule compositions (optionally mixed with suspending agents, preservatives, etc.) suitable for suspension. Suitable excipients are, for example, water, saline, dextrose, and so forth. Nontoxic auxiliary substances, such as wetting agents, buffers, lubricants, suspending agents, or emulsifiers may also be added. One specific useful formulation contains an effective amount of detergent, such as 0.1% sodium dodecyl sulfate (SDS), to effect solubility and bacteriostasis. One presently preferred injectable vehicle for administering microcapsules comprises an aqueous suspension of 2% carboxymethyl cellulose and 1% Tween ® 20.

Preferred compositions of the invention will deliver PEGylated hIL-2 (or an equivalent soluble form of hIL-2) at a controlled rate of about $10^3$ to $10^5$ units/Kg/day for a duration of 7 to 30 days. (Pure hIL-2 has a specific activity of about $3-6 \times 10^6$ U/mg.) The microcapsule formulation is a free-flowing powder consisting of relatively spherical particles 20 to 140 um in diameter that can be injected intramuscularly or subcutaneously with a conventional hypodermic needle, and the microcapsules contain 0.5 to 20% PEGyl-hIL-2 encapsulated in PLG with a release-modulating amount of HSA.

The regime of administration for shipping fever will depend on the conditions of shipment and the feedlot. It is preferred that administration be initiated prior to shipment, or at least as early as arrival on the feedlot and that the formulation provide for continuous release over a period of, for example, 14-30 or more days. The term "continuous" is intended to denote true continuous administration, such as is achieved via the sustained-release dosage form of the invention. Equivalent daily doses in the range of above about $10^3$ and below about $10^6$ units/Kg/day, preferably about $10^4$ to $10^5$ units/Kg/day, are generally used. In cattle, doses above about $10^6$ units/Kg/day begin to cause undesirable side effects.

For other livestock stress-induced or respiratory distress syndromes, the regime and amounts administered will depend on the nature and size of the animal (e.g., pig, goat, sheep, etc.) and on the severity of the symptoms. It is expected, however, that the effective dose for such syndromes will be in the same range (on a unit per weight basis) as that used for shipping fever.

Formulations of the invention may be administered alone or as a supplement to vaccines used to protect against stress-related diseases.

Similarly, it is not possible to set forth beforehand an effective dose of these formulations for treatment of cancer. The effective dose will depend upon the age and condition of the subject, its species, the nature and severity of the cancer, etc. However, these factors may be determined by one of ordinary skill in the art.

C. EXAMPLES

The following examples are intended to further support or illustrate but not to limit the invention.

Preparation 1

(Preparation of PLG Polymer)

PLG is prepared following the procedure set forth by D.R. Cowsar et al, *Meth Enzymol* (1985) 112:101–116, incorporated herein by reference. The procedure is essentially as follows:

This polymer is prepared by ring-opening polymerization of lactide and glycolide (cyclic lactone dimers of lactic acid and glycolic acid, respectively) to form a random copolymer. Glycolide and lactide may be obtained from commercial sources, or may be prepared by dimerizing glycolic or lactic acid, respectively, followed by pyrolysis to provide the closed-ring product. This process is illustrated below with glycolide.

Preparation of Glycolide

Excess water is distilled from 67% aqueous glycolic acid (450 g) in a 500 ml three-necked round bottom flask equipped with a heating mantle, distillation head, thermometer, and condenser. A water aspirator is used to reduce the pressure as the solution is boiled. After the excess water has distilled (ca. 150 g), the flask is heated to about 200° C. to remove additional water by dehydration of the glycolic acid. When water evolution ceases, the flask is allowed to cool to room temperature under vacuum. Next, $SbO_3$ (3 g) is added as a catalyst. The distillation head and condenser are removed, and the flask connected to two receiving flasks and a trap arranged in series. The receiving flasks and trap are cooled with dry ice/isopropanol baths, and the pressure reduced to 2 mmHg with a vacuum pump. The reaction flask is heated to 260°-280° C. to distill the crude glycolide. The material distilling between 110 and 130° C. is collected in the first receiving flask, to provide crude glycolide (about 195 g).

The crude glycolide is purified by pulverizing the mass and slurrying it with isopropanol (400 ml) at room temperature. The glycolide is collected by vacuum filtration, and thereafter protected from atmospheric moisture. The glycolide is combined with a volume of dry ethyl acetate (EtOAc, stored over molecular sieves) equal to 75% of its weight, heated to reflux to dissolve the monomer, cooled slowly to room temperature, and then cooled in an ice bath until crystallized. The monomer is recrystallized in this manner three times, and is collected in a glove box under dry $N_2$. After the final recrystallization, the product is dried at room temperature under <2 mmHg vacuum in a desiccator, to yield about 120 g of pure (>99.5% van't Hoff purity by differential scanning calorimetry - DSC) glycolide, m.p. 82°-84° C.

Preparation of DL-Lactide

Crude DL-lactide may be purchased from commercial suppliers, and is purified as follows:

Crude DL-lactide (200 g) is combined with EtOAc (200 ml) in a beaker, and the mixture gently heated on a stirring hot plate to dissolve the lactide. The hot mixture is then quickly filtered through an extra-coarse sintered glass frit to remove insoluble material. The filtered solution is then distilled under vacuum to reduce the solvent volume to about half the weight of the lactide. The filtered material is then allowed to cool slowly to room temperature, and then cool for an additional 2 hours in an ice bath. The product is collected by vacuum filtration in a glove box under $N_2$, and the recrystallization from EtOAc repeated three more times (without glass frit filtration). After the final recrystallization, the product is collected by vacuum filtration and dried at room temperature in a desiccator under vacuum (about 2 mmHg). The purified lactide is characterized and stored in an oven-dried glass jar in a desiccator until needed. The final yield is about 125 g, m.p. 124-126° C. Purity is >99.5% by DSC.

Copolymerization

The po-ymerization apparatus is a 300 ml three-neck round bottom flask, equipped with a mechanical stirrer and a gas inlet tube. All glassware is oven-dried overnight at 150° C. and cooled under dry $N_2$. All manipulations are conducted in a glove box under dry $N_2$. Pure glycolide (9.9 g) and DL-lact.d:e (90.1 g) are added to the flask (mol %=12%/88%) and heated at 140°-145° C. using an oil bath until the monomers are partially melted. The monomers are stirred with the flask under positive $N_2$ pressure until completely melted. Then, stannous octoate (0.05 mol %) is added to catalyze the ring-opening polymerization reaction. The mixture is stirred for about 30 minutes, at which point it becomes too viscous to stir. The stirrer is then lifted from the mixture, and the mixture heated without stirring for an additional 16-18 hours. The product is then cooled to room temperature, and the flask broken away. The lump of polymer is then submerged in liquid nitrogen, and any remaining glass removed. While still cold, the polymer is then broken into smaller chunks, dissolved in $CH_2Cl_2$ (800 ml), filtered through a sintered glass filter, and precipitated in excess methanol. The precipitate is dried in vacuo at 30°-40° C., ground in a Wiley Mill, characterized, and stored over Drierite ®, yielding about 90 g of polymer.

The product exhibits an inherent viscosity of 0.6 to 0.8 dl/g (0.5 g/dl in $CHCl_3$ at 30° C.). The ratio of monomers in the random copolymer is 85-86% lactide, 14-15% glycolide, as may be determined by NMR in 50:50 hexafluoroacetone:trifluoroacetic acid.

EXAMPLE 1

(In Vitro Activity)

Figure 2B:
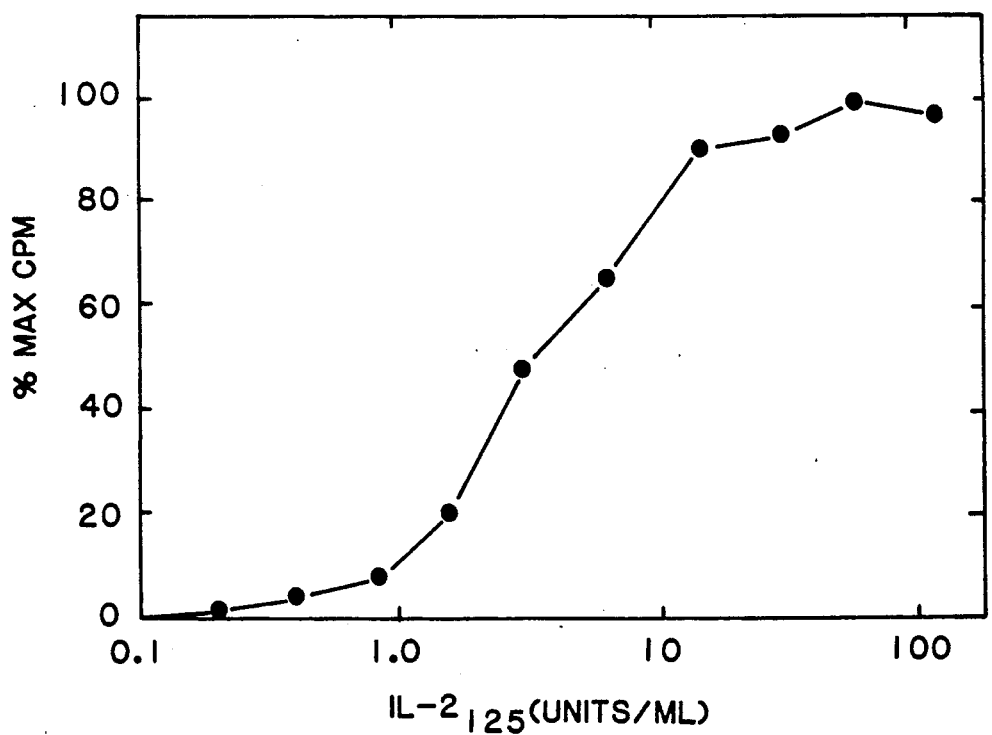
Figure 4B:
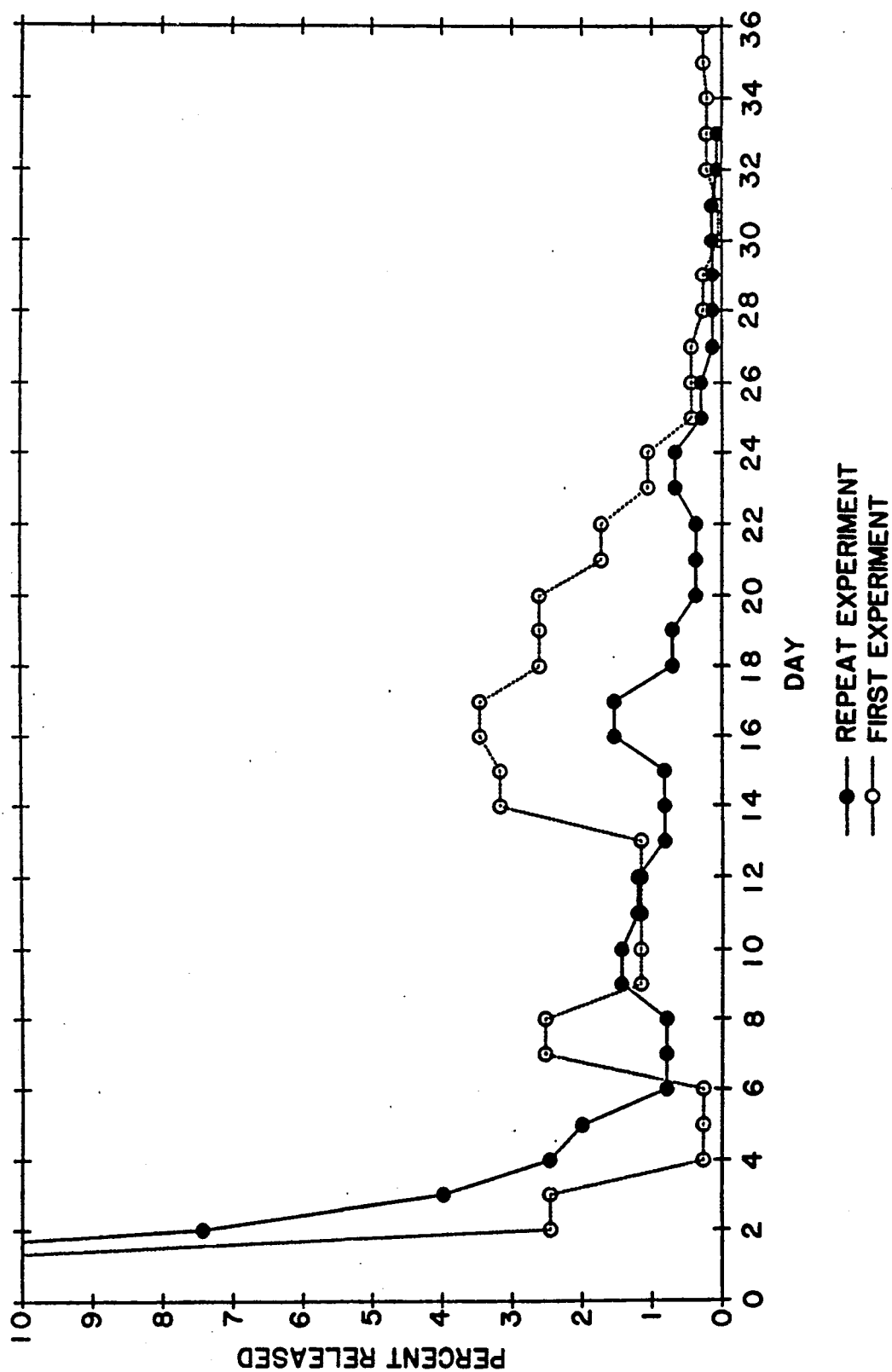
Figure 4D:
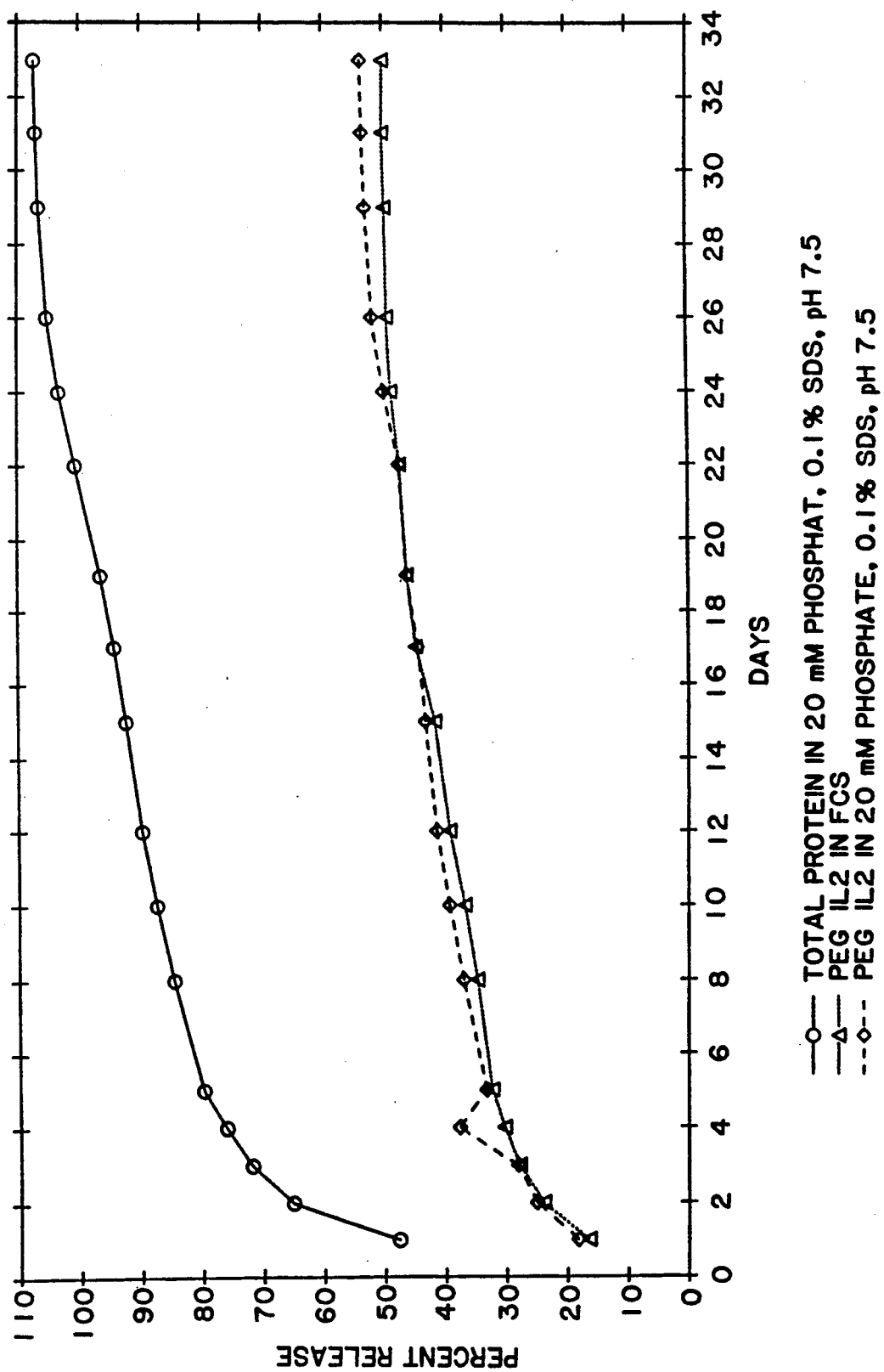

In vitro activity with respect to bovine and porcine peripheral blood mononuclear cells (PBMC) has been shown for recombinant hIL-2 (S. Fong et al, *Vet Immunol and Immunopathol* (1986) 11:91–100, incorporated herein by reference). The hIL-2 used in this work is designated des-ala$_1$ser$_{125}$rIL-2, lacks an initial alanine, and has a serine rather than a cysteine at position 125. It was shown to be mitogenic for unactivated bovine and porcine PBMC, and to be able to maintain the long-term growth of ConA activated PBMC from both species. FIGS. 2A and 2B are curves showing the dose-response of ConA-activated bovine (2A) and porcine (2B) PBMC to des-ala$_1$-ser$_{125}$rIL-2. Also, bovine and porcine PBMC preincubated with des-ala$_1$ser$_{125}$rIL-2 for 1-5 days showed enhanced cytotoxicity against tumor cell targets.

In addition, J.L. Stott et al, *Vet Immunol & Immunopath*, (1986) 13:31–36 (incorporated herein by reference) have shown that bovine and porcine peripheral blood lymphocytes were responsive to human recombinant IL-2 in lymphocyte blastogenesis assays. Blastogenesis was determined by incorporation of $^3$H-thymidine (18 hr pulse) in 4-day lymphocyte cultures, and the results expressed as the log$_{10}$ of the geometric mean ($G_x$) of disintegrations per minute (DPM)/culture and plotted by nonlinear regression analysis as shown in FIG. 3. Mitogen dilution and concentration of hIL-2 in units are shown on the X-axis. These results show that the effect of hIL-2 on bovine and porcine cells is comparable to that shown by the plant lectins PHA and ConA, which are known to stimulate blastogenesis.

EXAMPLE 2

(Potentiation of Cell-Mediated Immunity)

Because respiratory diseases are predominantly controlled by the cellular (T-cell) immune system, the ability of hIL-2 to boost the cellular immune response in livestock is indicative of its effectiveness against these symptomologies. In vivo injections of recombinant hIL-2 produced elevated levels of lymphocyte blastogenesis in the blood of calves.

Specifically, eight calves weighing 135–225 Kg (3–5 months old) were randomly sorted into 4 groups of 2 each which received weekly injections for one month as follows: Groups 1, 2, and 3 received $10^4$, $10^5$, and $10^6$ units/Kg, respectively, intramuscularly; group 4 received only excipient. The animals were assessed for lymphocyte stimulation. The results show that resting lymphocyte activity was elevated by the recombinant hIL-2 treatment as determined by blastogenesis assays performed prior to each inoculation over the period in calves receiving $10^5$ and $10^6$ units/Kg only. For calves receiving $10^5$ units/Kg, lymphocyte activity returned to normal within two weeks following the last IL-2 administration; $10^6$ units/Kg-injected calves remained elevated at that time.

EXAMPLE 3

(Treatment With Non-encapsulated IL-2)

Two hundred heifers were purchased from several different sources in Tennessee and transported to a research feedlot in Colorado. The average weight of the animals was approximately 400 lbs (180 Kg). The animals were segregated randomly (weight and breed) into four groups, designated I through IV.

Recombinant hIL-2 (des-ala$_1$ser$_{125}$rhIL-2) was formulated in 0.05% SDS and administered intramuscularly to the animals upon entry to the feedlot. All animals were treated daily, five times per week, for two weeks. The dose protocols for the four groups were as follows.

| Group | IL-2 Dose (U/kg/day) |
|---|---|
| I | $2 \times 10^4$ (high dose) |
| II | $2 \times 10^3$ (mid dose) |
| III | $2 \times 10^2$ (low dose) |
| IV | control (diluent) |

The animals did not receive standard BRDS-related vaccination. They were, by chance, subjected to severe snow and cold weather during their first days on the feedlot, and accordingly, were placed on silage feed early on. The health of the animals was observed on a daily basis by personnel blind to experimental treatment. The animals were weighed at regular intervals. Table 1 reports the results of the treatment as of day 21.

TABLE 1

| Mortality | Number Dead/Total | |
|---|---|---|
| Control | 21/50 | |
| Low Dose | 20/50 | p = 0.839 |
| Mid Dose | 26/50 | p = 0.316 |
| High Dose | 14/50 | p = 0.142 |
| Incidence of Disease | Number Sick or Dead/Total | |
| Control | 43/50 | |
| Low Dose | 42/50 | p = 0.779 |
| Mid Dose | 43/50 | p = 1.000 |
| High Dose | 38/50 | p = 0.202 |
| Severity of Disease | Average Daily Severity of Group (Score 0-3; Death = 4) | |
| Control | 1.76 | |
| Low Dose | 1.79 | p = 0.950 |
| Mid Dose | 1.93 | p = 0.395 |
| High Dose | 1.38 | p = 0.052 |

Morbidity and mortality rates during the study were higher than expected. As reported some groups showed 85% morbidity and 50% mortality. Sickness was observed as early as two days into the study. Several factors may have been responsible for the extreme severity of BRDS seen in this study: the severe snow and cold weather; the animals were 'light-weight' (400 lbs avg) and 'thin-skinned' (from Tennessee); groups have been 'put-together' from several sources (thus, they were not 'fresh' and many had seen several salebarns prior to shipping to Colorado); and the animals were placed on silage feed early on, and may have been eating poorly.

In the clinical judgment of the personnel observing the health of the animals, the high-dose IL-2 group consistently "looked better". This is supported by the data in Table 1 in which the high-dose IL-2 group showed a consistent trend towards decreased mortality, decreased incidence of disease, and decreased severity of disease.

In all cases, the high-dose group performed better than the control group. Although the statistical significance of these differences (p-value), is marginal (using the strict definition of significance, p<0.05), all results are consistent.

Additional measures not presented in Table 1 also supported the trend toward efficacy in the high-dose IL-2 group. For instance, animals in the high-dose IL-2 group which died did so later in the study than did control animals.

As of day 21, there were no differences in the weight of the surviving animals. There were, however, significant differences in the total payweight per group, since more animals survived in the high-dose group.

EXAMPLE 4

(Preparation of Microcapsules)

PLG microcapsules containing PEGyl-IL-2+HSA were prepared as follows:

PLG (1.0003 g), was prepared as in Preparation 1, but with a lactide:glycolide ratio of 52:48 (inherent viscosity 0.73 dL/g, in hexafluoroisopropanol at 30° C. using a Cannon viscometer). Then, PLG (0.5006 g) was weighed into a glass sample vial (6 mL), followed by $CH_2Cl_2$ (3 7 mL). The vial was sealed, and the polymer allowed to dissolve, providing a 12% solution. Next, a 1:20 mixture of IL-2+HSA (0.1256 g) was weighed into a 16×75 mm test tube. The PLG solution was added to the test tube, and the mixture homogenized three times for 30 sec, with 15 sec intervals between homogenations. The homogenized mixture was then transferred to a 200 mL kettle containing 6.0% aqueous poly(vinyl alcohol) (150 mL) saturated with $CH_2Cl_2$ (2.4 mL) with stirring at 1000 rpm, providing a stable oil-in-water emulsion. The kettle contents were stirred for 5 minutes, then poured into deionized water (10 L), with stirring at 800 rpm. Stirring was continued for 15 minutes to remove $CH_2Cl_2$. The resulting microcapsules were collected over an 8-in diameter 45 um stainless steel sieve, washed with deionized water (4 L), and dried for 48 hours in a vacuum chamber at room temperature.

EXAMPLE 5

(Comparison of Formulations)

Compositions of the invention were prepared as described above, and their in vitro release rates compared with other formulations, demonstrating the surprising efficacy of the invention.

The test formulations were as follows:

| # | Active Compound | Excipient | Ratio |
|---|---|---|---|
| 1. | PEGyl-IL-2 | HSA | 1:20 |
| 2. | PEGyl-IL-2 | HSA | 1:20 |
| 3. | PEGyl-IL-2 | HSA | 1:1 |
| 4. | PEGyl-IL-2 | mannitol | 1:20 |
| 5. | PEGyl-IL-2 | CMC | 1:20 |
| 6. | PEGyl-IL-2 | HPC | 1:20 |
| 7. | PEGyl-IL-2 | HES | 1:20 |
| 8. | PEGyl-IL-2 | PVA | 1:20 |
| 9. | PEGyl-IL-2 | PVP | 1:20 |
| 10. | PEGyl-IL-2 | PEG | 1:20 |
| 11. | PEGyl-IL-2 | none | NA |
| 12. | IL-2 | HSA | 1:20 | where CMC = carboxymethyl cellulose,
HPC = hydroxypropyl cellulose,
HES = hydroxyethyl starch,
PVA = poly(vinylalcohol), and
PVP = polyvinylpyrrolidone.

Formulations containing HPC, CMC, or PVA would not disperse in $CH_2Cl_2$, preventing formation of microcapsules. Thus, formulations 5, 6, and 8 were dropped from the remainder of the comparison. Each of the remaining formulations was loaded into PLG microcapsules as described in Example 4. Samples of each microcapsule formulation were assayed for protein content by the method of Lowry. The results were as follows:

| | Formulation | Protein % | IL-2 % |
|---|---|---|---|
| 1. | PEGyl-IL-2 + HSA | 14.2 | 0.68 |
| 2. | PEGyl-IL-2 + HSA | 6.6 | 0.31 |
| 3. | PEGyl-IL-2 + HSA (1:1) | 12.4 | 6.2 |
| 4. | PEGyl-IL-2 + mannitol | 1.8 | 1.8 |
| 5. | PEGyl-IL-2 + CMC | — | — |
| 6. | PEGyl-IL-2 + HPC | — | — |
| 7. | PEGyl-IL-2 + HES | 1.4 | 1.4 |
| 8. | PEGyl-IL-2 + PVA | — | — |
| 9. | PEGyl-IL-2 + PVP | 1.5 | 1.5 |
| 10. | PEGyl-IL-2 + PEG | 1.5 | 1.5 |
| 11. | PEGyl-IL-2 | 10.4 | 10.4 |
| 12. | IL-2 + HSA | 15.6 | 0.74 |

Each microcapsule formulation was tested in two media: fetal calf serum (FCS) at 37° C., or in SDS buffer (20 mM phosphate, pH 7.5, 0.1% SDS) at 37° C. FCS was chosen as a suitable analog to the in vivo environment that the formulation encounters upon actual administration, while the SDS experiment was performed as a measure of available protein. Samples (10 mg) were added to 1 mL of FCS or SDS in 1-2 mL Eppendorf tubes, and allowed to incubate for 30-50 days. Aliquots were withdrawn periodically and assayed (via bioactivity or Lowry assay) for IL-2 activity in the supernatant.

The results are shown in FIGS. 4-12. FIGS. 4A and 4C show release of PEGyl-IL-2 from formulation 1 in percent per day and cumulative percent per day. The data shows a high initial burst followed by a continuous daily release rate of about 2% up to day 28 for release in SDS. In FCS, the release is nearly identical, apart from an anomalous interruption on days 4-6. (This is possibly explained by the fact that the release rate for days 4-6 was determined by biological assay from an aliquot drawn on day 6: an error in the assay would thus affect the data for all three days.) FIGS. 4B and 4D show the results of a repeat experiment with formulation 1 (no interruption).

Figure 5B:
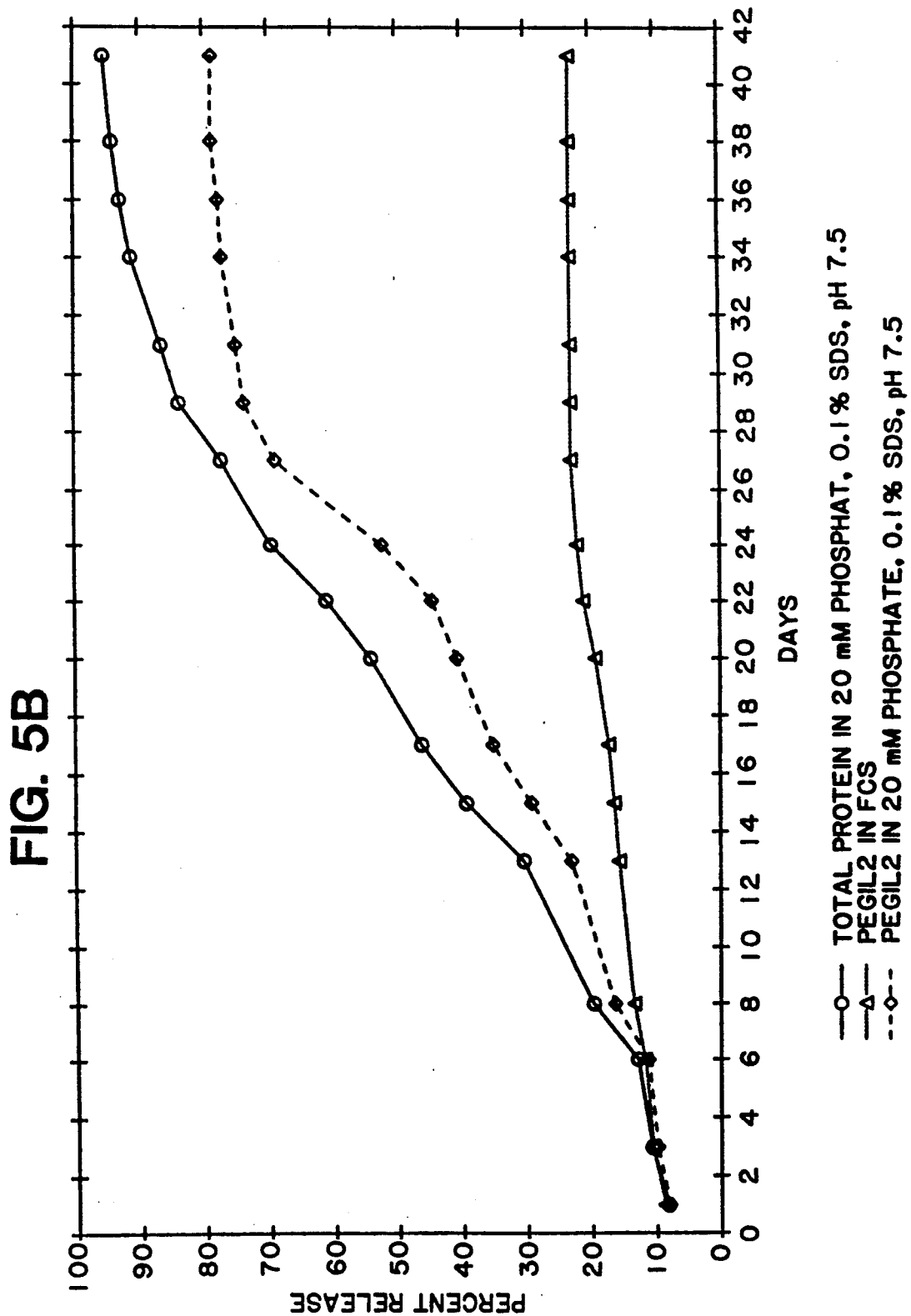

FIGS. 5A and 5B show release of PEGyl IL-2 from formulation 2 in percent per day and cumulative percent per day. The data shows that in SDS, an 8% initial burst is followed by an induction period (<1%/day) days 2-6, followed by release at 1-3% up to day 34. However, release in FCS was characterized by an initial burst, followed by very low (0.2%-1%) release up to day 27. The total release in FCS was only about 20%.

FIGS. 6A and 6B show release of PEGyl IL-2 from formulation 3 in percent per day and cumulative percent per day. The data shows that in SDS, a high initial burst is followed by continuous release of 1-5%/day up to day 30. However, in FCS, the high initial burst is followed by an induction period (<1%) until day 10, followed by release of 1-8%/day until day 18, followed by <1%/day through day 30. Only about 56% is released in FCS.

FIGS. 7A and 7B show release of PEGyl-IL-2 from formulation 4 in percent per day and cumulative percent per day. The data shows that in both media release is characterized by an initial burst, a 9-11 day induction period, and low release (0.5-0.7%/day) thereafter. Only about 38% (in SDS) and 20% (in FCS) of the PEGyl-IL-2 was released.

FIGS. 8A and 8B show release of PEGyl-IL-2 from formulation 7 in percent per day and cumulative percent per day. The data, similar to formulation 4, depicts an initial burst responsible for nearly all of the PEGyl-IL-2 released, followed by very low release rates thereafter. In SDS, a minor release peak (days 17-23) of about 1-2%/day was observed, however total release was less than about 20% for SDS and FCS.

Figure 9B:
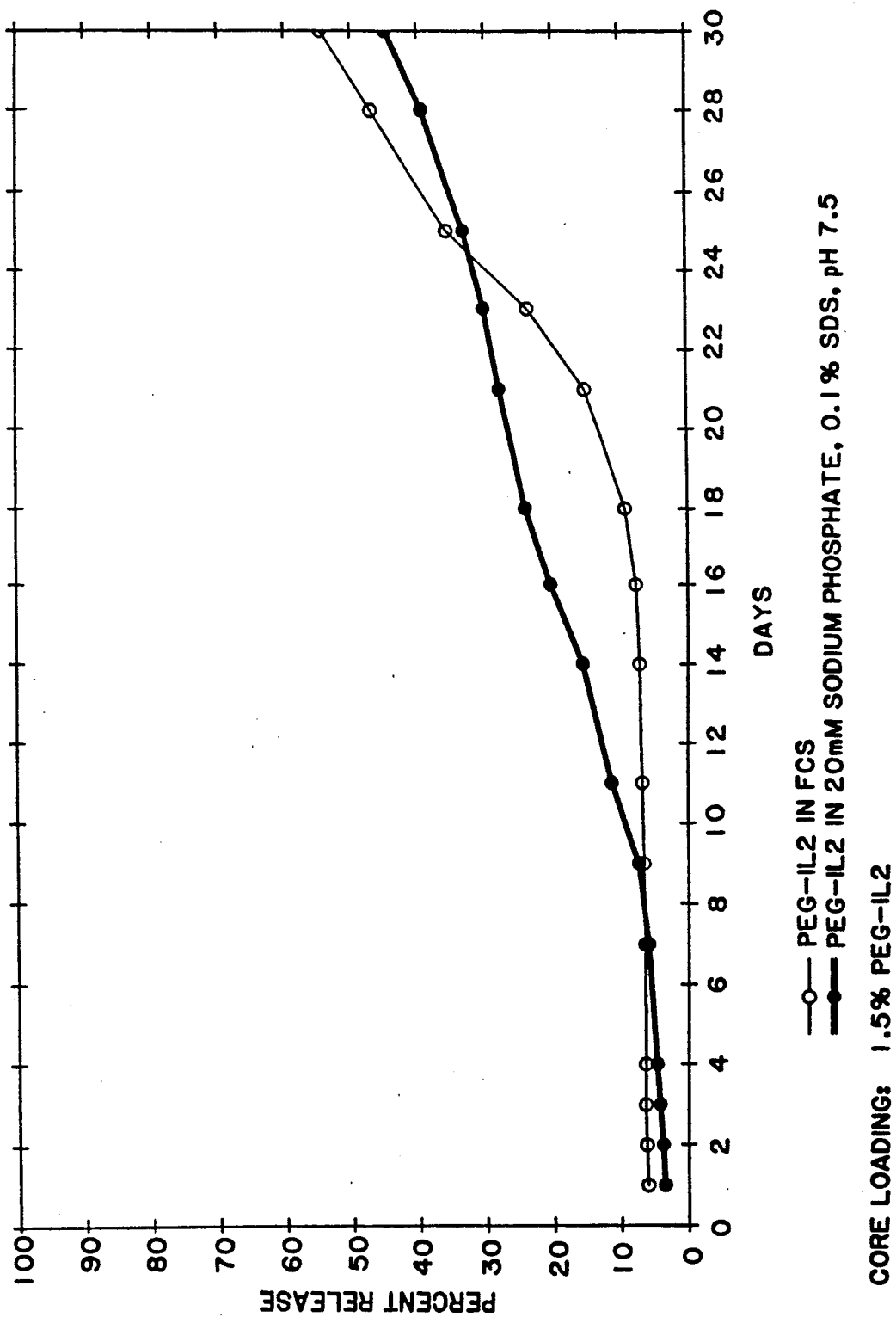

FIGS. 9A and 9B show release of PEGyl-IL-2 from formulation 9 in percent per day and cumulative percent per day. The data shows that in SDS, a high initial pulse is followed by an induction period of 7-9 days, followed by release at about 1-3%/day. In FCS, the induction period is about 16-18 days, followed by release at about 1-6%/day, tailing off at day 30. Only 45 and 53% of the PEGyl-IL-2 is released by day 30.

FIGS. 10A and 10B show release of PEGyl-IL-2 from formulation 10 in percent per day and cumulative percent per day. The data shows that in SDS, the initial burst is followed by a 16-day induction period, followed by release at 1-3%/day for days 17-25. In FCS, a very low release rate (<0.5%/day) occurs after the initial release. The total PEGyl-IL-2 released was about 30% and 18%.

FIGS. 11A and 11B show release of PEGyl-IL-2 from formulation 11 in percent per day and cumulative percent per day, contrasted with the release rates for formulations 1 (at a core loading of 11.3%) (diamonds) and 3 (triangles) in SDS. The data shows that formulations 11 and 3 exhibit induction periods of 11 and 14 days, followed by release at 1-8%/day. Formulation 1 exhibited a slow decline to 1% at days 8-9, followed by a release rate of 1-4%/day for the remainder of the study. The total PEGyl-IL-2 released was about 57% for formulations 11 and 3, and about 85% for formulation 1.

Figure 12B:
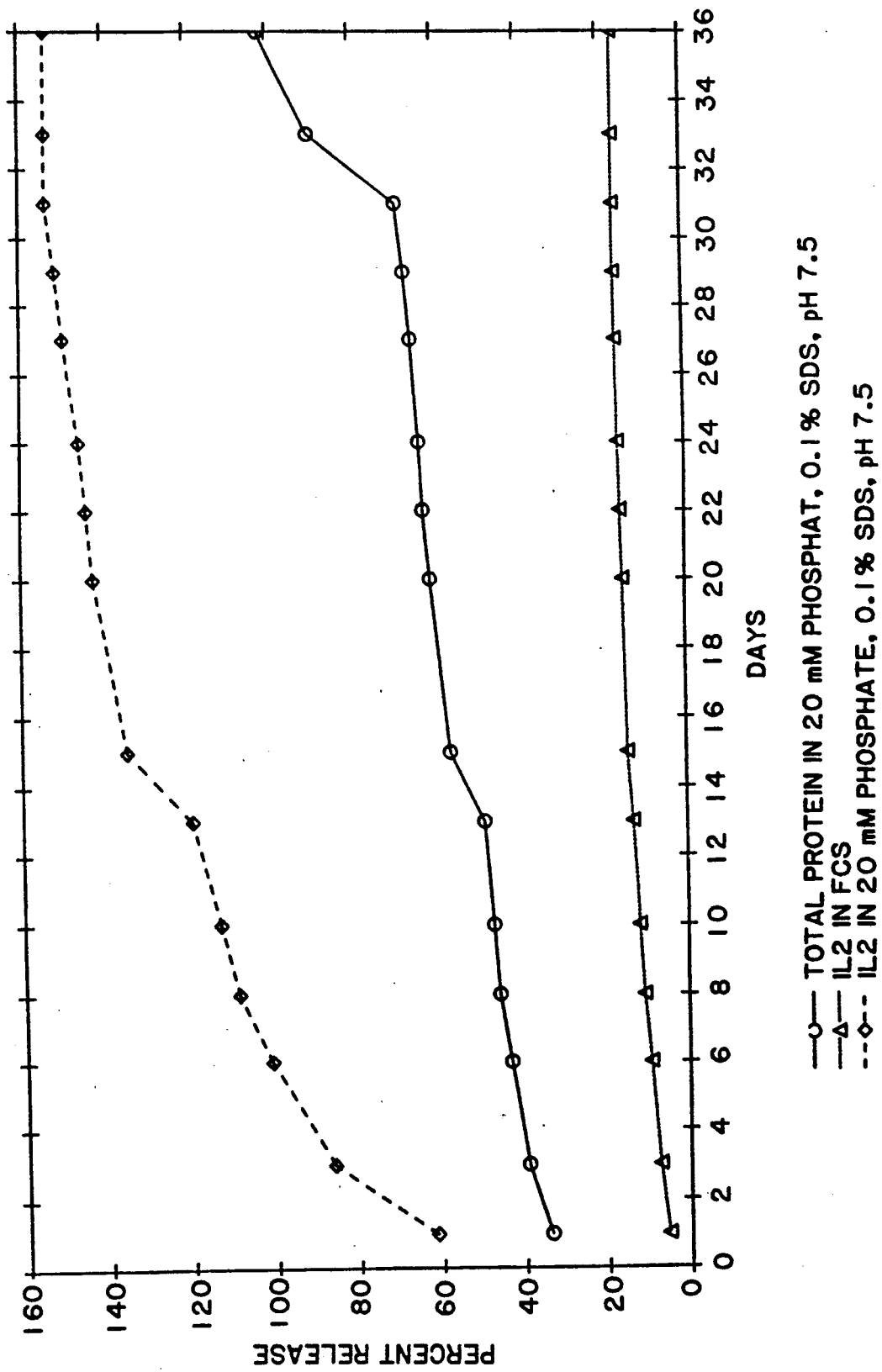

FIGS. 12A and 12B show release of IL-2 from formulation 12 in percent per day and cumulative percent per day. The data shows that in SDS, and exponential decline to 2%/day occurs in the first 13 days, followed by release at about 2-8%/day up to day 21, after which release fails to exceed about 1.5%/day. In FCS, the initial release is followed by release of less than 1%/day for the remainder of the test period. The IL-2 was completely released in SDS, but only about 18% released in FCS.

The data are summarized below.

TABLE

| | Release in FCS at 37° C. | | | |
|---|---|---|---|---|
| | Formulation | Ratio | Induction | Total % |
| 1. | PEGyl-IL-2 + HSA | 1:20 | 0 | 50 |
| 2. | PEGyl-IL-2 + HSA | 1:20 | 6 | 20 |
| 3. | PEGyl-IL-2 + HSA | 1:1 | 10 | 56 |
| 4. | PEGyl-IL-2 + mannitol | 1:20 | * | 20 |
| 5. | PEGyl-IL-2 + CMC | 1:20 | — | — |
| 6. | PEGyl-IL-2 + HPC | 1:20 | — | — |
| 7. | PEGyl-IL-2 + HES | 1:20 | * | 16 |
| 8. | PEGyl-IL-2 + PVA | 1:20 | — | — |
| 9. | PEGyl-IL-2 + PVP | 1:20 | 18 | 53 |
| 10. | PEGyl-IL-2 + PEG | 1:20 | * | 18 |
| 11. | PEGyl-IL-2 | NA | 11 | 57 |
| 12. | IL-2 + HSA | 1:20 | * | 18 |

Induction (<1%/day) in days.
* = No substantial release after initial burst

Thus, the data demonstrate that the goals of substantial daily release (1-3%/day), substantial total release, and lack of induction times are achieved only using a composition of the invention.

EXAMPLE 6

(Formulations)

Suitable formulations for administering microencapsulated PEGyl-IL-2+HSA are prepared as follows:

(A) Intramuscular injection

| | |
|---|---|
| Microcapsules | 900.0 mg |
| Carboxymethyl cellulose | 2.0 mg |
| Tween ® 20 | 1.0 mg |
| Sterile PBS qs | 2.0 mL |

Microcapsules containing PEGyl-IL-2+HSA are prepared as detailed in Example 4. The carboxymethyl cellulose (CMC) and Tween ® 20 are dissolved in sterile PBS, and the microcapsules added with vigorous stirring. The resulting suspension is suitable for administration to one 180 Kg bovine.

(B) Solid Formulation

A dry solid formulation for reconstitution as an injectable suspension is prepared as follows:

| | |
|---|---|
| Microcapsules | 900.0 mg |
| Carboxymethyl cellulose | 2.0 mg |
| SDS | 1.0 mg |
| Lactose | 1.0 g |

The components are mixed together as dry powders. Alternatively, the components may be suspended/dissolved in water, and the suspension lyophilized to provide a reconstitutable microcapsule suspension.

(C) Solid Bolus

The first stomach (rumen) of ruminants is an organ of microbial cellulose fermentation rather than acid digestion. The rumen's contents are essentially neutral in pH. Accordingly, it is expected that oral administration of microcapsules to ruminants will be effective as long as the microcapsules can be immobilized within the rumen. A suitable bolus is prepared as follows:

A stainless steel cylinder 5 cm long by 2.5 cm diameter is sealed at one end using a steel plug which seats firmly by press-fitting. The composition of part B above is then packed into the cylinder against the inner surface of the plug, and the open end sealed using a nylon 66 membrane having 5 um pores.

What is claiemd is:

1. A composition for continuously delivering a relatively constant, effective amount of PEGyl-IL-2 comprising:
PEGyl-IL-2 with a release-modulating amount of human serum albumin, encapsulated in poly(lactide-co-glycolide) microcapsules.

2. The composition of claim 1 wherein said PEGyl-IL-2 is present with said HSA in a ratio of about 1:5 to 1:30.

3. The composition of claim 2 wherein said microcapsules contain 5-20% PEGyl-IL-2+HSA.

4. A formulation for administering IL-2 or an IL-2 equivalent continuously over a period of 14-30 days, which formulation comprises:
PEGyl-IL-2 mixed with a release-modulating amount of human serum albumin, encapsulated in poly(lactide-co-glycolide) microcapsules; and
a liquid, pharmaceutically acceptable excipient capable of suspending said microcapsules.

5. The formulation of claim 4, wherein said formulation comprises only components acceptable for parenteral administration.

6. The composition of claim 1 wherein said PEGyl-IL-2 is released over 7-30 days.